US010653309B2

(12) United States Patent
Shimozato et al.

(10) Patent No.: US 10,653,309 B2
(45) Date of Patent: May 19, 2020

(54) OPHTHALMOLOGIC APPARATUS, AND OPHTHALMOLOGIC IMAGING METHOD

(71) Applicant: CANON KABUSHIKI KAISHA, Tokyo (JP)

(72) Inventors: Yuki Shimozato, Tokyo (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 13 days.

(21) Appl. No.: 15/837,367

(22) Filed: Dec. 11, 2017

(65) Prior Publication Data

US 2018/0160897 A1 Jun. 14, 2018

(30) Foreign Application Priority Data

Dec. 13, 2016 (JP) ................. 2016-241022

(51) Int. Cl.
*A61B 3/10* (2006.01)
*A61B 3/00* (2006.01)
*A61B 3/12* (2006.01)
*A61B 5/00* (2006.01)
*G01B 9/02* (2006.01)

(52) U.S. Cl.
CPC ............ *A61B 3/102* (2013.01); *A61B 3/0008* (2013.01); *A61B 3/0025* (2013.01); *A61B 3/1225* (2013.01); *A61B 5/746* (2013.01); *G01B 9/02063* (2013.01); *G01B 9/02064* (2013.01); *G01B 9/02067* (2013.01)

(58) Field of Classification Search
CPC ..... A61B 3/102; A61B 3/0025; A61B 3/1225; A61B 5/746; A61B 3/0008; G01B 9/02067; G01B 9/02063; G01B 9/02064
See application file for complete search history.

(56) References Cited

U.S. PATENT DOCUMENTS

| 8,804,127 B2 | 8/2014 | Shimoyama et al. |
| 8,960,904 B2 | 2/2015 | Aoki et al. |
| 8,960,905 B2 | 2/2015 | Aoki et al. |
| 8,970,849 B2 | 3/2015 | Sakagawa et al. |
| 9,022,569 B2 | 5/2015 | Nakahara et al. |

(Continued)

FOREIGN PATENT DOCUMENTS

| JP | 2009-291252 A | 12/2009 |
| WO | 2014/203901 A1 | 12/2014 |

OTHER PUBLICATIONS

May 30, 2018 European Search Report in European Patent Appln. No. 17002023.4.

(Continued)

*Primary Examiner* — Jack Dinh
(74) *Attorney, Agent, or Firm* — Venable LLP

(57) ABSTRACT

Provided is an ophthalmologic apparatus including: an acquisition unit configured to acquire tomographic information of an eye to be examined using information on interference light between return light from the eye to be examined, which is irradiated with measurement light, and reference light; and a vitreous structure detection unit configured to detect a vitreous structure of the eye to be examined using tomographic information of the eye to be examined that is acquired after at least one of the difference in optical path length between the measurement light and the reference light and the in-focus position is controlled, wherein the acquisition unit is configured to acquire tomographic information of the vitreous structure.

21 Claims, 20 Drawing Sheets

(56) References Cited

U.S. PATENT DOCUMENTS

| | | |
|---|---|---|
| 9,295,382 B2 | 3/2016 | Sakagawa |
| 9,326,681 B2 | 5/2016 | Shimozato |
| 9,392,936 B1 | 7/2016 | Yu et al. |
| 2012/0140173 A1 | 6/2012 | Uhlhorn et al. |
| 2014/0257076 A1 | 9/2014 | Shimozato |
| 2015/0297077 A1 | 10/2015 | Shimozato et al. |
| 2017/0027443 A1 | 2/2017 | Sakagawa et al. |

OTHER PUBLICATIONS

Mar. 19, 2020 Japanese Official Action in Japanese Patent Appln. No. 2016-241022.

OPHTHALMOLOGIC APPARATUS, AND OPHTHALMOLOGIC IMAGING METHOD

BACKGROUND OF THE INVENTION

Field of the Invention

The present invention relates to an ophthalmologic apparatus, and an ophthalmologic imaging method.

Description of the Related Art

As ophthalmologic apparatus configured to take a tomographic image of an eye to be examined, apparatus using optical coherence tomography (OCT) (hereinafter referred to as "OCT apparatus") have been known. An OCT apparatus is an apparatus configured to irradiate the eye to be examined with low-coherent light (measurement light), and obtain tomographic information of the eye to be examined using interference light obtained by combining return light from the eye to be examined with reference light. The OCT apparatus can acquire the tomographic image by scanning the low-coherent light over a fundus of the eye to be examined. Therefore, the OCT apparatus is widely used in diagnosis of a retina and other uses.

In acquiring the tomographic image of the fundus, a focus position and a coherence gate position are adjusted to a retina position of the eye to be examined in the OCT apparatus. The "coherence gate position" as used herein refers to a position at which optical path lengths of the measurement light and the reference light are equal to each other, and in the OCT apparatus, an imaging position of the tomographic image in a depth direction is determined depending on the coherence gate position. The imaging position is a position at which the optical path length of the measurement light is equal to the optical path length of the reference light on an optical path of the measurement light, and generally corresponds to an imaging position at an upper edge or a lower edge of the tomographic image taken by the OCT apparatus. The coherence gate position may be moved by changing the optical path length of the measurement light or the reference light to change a difference in optical path length between the measurement light and the reference light.

Regarding the adjustments of the focus position and the coherence gate position to the retina position of the eye to be examined, in Japanese Patent Application Laid-Open No. 2009-291252, there are disclosed adjustments of a focus position and a coherence gate position to a retina position of a fundus using a front image or a tomographic image of the fundus.

SUMMARY OF THE INVENTION

According to one embodiment of the present invention, there is provided an ophthalmologic apparatus including: an acquisition unit configured to acquire tomographic information of an eye to be examined using information on interference light between return light from the eye to be examined, which is irradiated with measurement light, and reference light; an optical path length difference controlling unit configured to control a difference in optical path length between the measurement light and the reference light; an in-focus position controlling unit configured to control an in-focus position of the measurement light; and a vitreous structure detection unit configured to detect a vitreous structure of the eye to be examined using tomographic information of the eye to be examined that is acquired after at least one of the difference in optical path length and the in-focus position is controlled, wherein the acquisition unit is configured to acquire tomographic information of the vitreous structure.

According to another embodiment of the present invention, there is provided an ophthalmologic imaging method including: acquiring tomographic information of an eye to be examined using information on interference light between return light from the eye to be examined, which is irradiated with measurement light, and reference light; detecting a vitreous structure of the eye to be examined using tomographic information of the eye to be examined that is acquired after at least one of a difference in optical path length between the measurement light and the reference light, and an in-focus position of the measurement light is controlled; and acquiring tomographic information of the vitreous structure.

Further features of the present invention will become apparent from the following description of exemplary embodiments with reference to the attached drawings.

DESCRIPTION OF THE EMBODIMENTS

Figure 1:
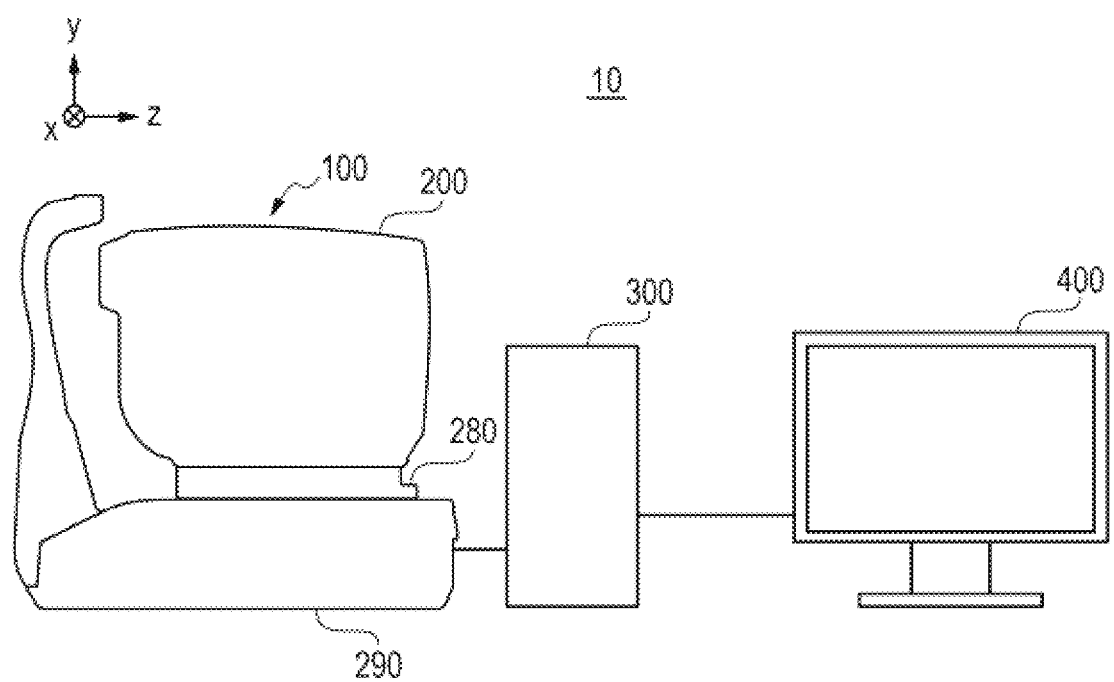
FIG. 1 is a diagram for illustrating a schematic configuration of an OCT apparatus according to a first embodiment of the present invention.

In recent years, with the progress of the OCT technology, not only a retina but also a vitreous body of an eye to be examined can now be imaged under predetermined conditions. Meanwhile, it is known that the vitreous body changes and liquefies with aging. It is also known that the vitreous body undergoes a change in tissue due to a disease and other causes. The vitreous body is generally a clear and colorless jelly-like substance, and does not appear in an OCT tomographic image. However, a portion undergoing the change in tissue as described above scatters or reflects measurement light, and hence can be imaged by OCT. The portion of the vitreous body that is undergoing the change in tissue and can be imaged by OCT is hereinafter referred to as "vitreous structure".

The change in tissue of the vitreous body may damage the retina or cause a damage in the vitreous body itself. Therefore, it is desired to image the vitreous structure more clearly. However, OCT has a small depth of focus, and hence in a state in which a focus position is adjusted to a retina position of a fundus, the vitreous structure is blurred, and is not imaged very clearly. Moreover, depending on a degree of posterior vitreous detachment and other factors, a position of the vitreous structure with respect to the retina varies greatly among individuals, and hence with normal adjustment in which a coherence gate position is adjusted to the retina position of the fundus, there may be a case in which a necessary part of the vitreous structure is not imaged.

Exemplary embodiments of the present invention have been made in view of the above-mentioned problem, and therefore have an object to appropriately image the vitreous structure of the eye to be examined.

To this end, one of ophthalmologic apparatus according to the exemplary embodiments includes an acquisition unit, which is configured to acquire tomographic information of an eye to be examined using information on interference light. The one of the ophthalmologic apparatus according to the exemplary embodiments includes a vitreous structure detection unit, which is configured to detect the vitreous structure of the eye to be examined using tomographic information of the eye to be examined that is acquired after at least one of a difference in optical path length between measurement light and reference light, and an in-focus position is controlled. The one of the ophthalmologic apparatus according to the exemplary embodiments is configured to acquire tomographic information of the vitreous structure.

In other words, one of the ophthalmologic apparatus according to the exemplary embodiments is configured to control at least one of the difference in optical path length and the in-focus position such that the vitreous structure of the eye to be examined is detected. As a result, according to the one of the exemplary embodiments, the vitreous structure of the eye to be examined can be imaged appropriately.

Preferred embodiments of the present invention will now be described in detail in accordance with the accompanying drawings. It should be noted, however, that dimensions, materials, shapes, and relative positions of components to be described in the embodiments below are exemplary, and may be changed depending on a configuration of an apparatus to which the present invention is applied, or on various conditions. Moreover, throughout the drawings, like reference symbols are used thereamong to denote like or functionally similar elements.

First Embodiment

Now, as an example of an ophthalmologic apparatus used for ophthalmologic imaging according to a first embodiment of the present invention, an OCT apparatus 10 is described with reference to FIG. 1 to FIG. 11C. The OCT apparatus 10 according to the first embodiment is configured to search for a vitreous structure by sequentially moving an OCT focus position and a coherence gate position, and to adjust appropriate imaging parameters for the detected vitreous structure.

Schematic Configuration of OCT Apparatus

Figure 2:
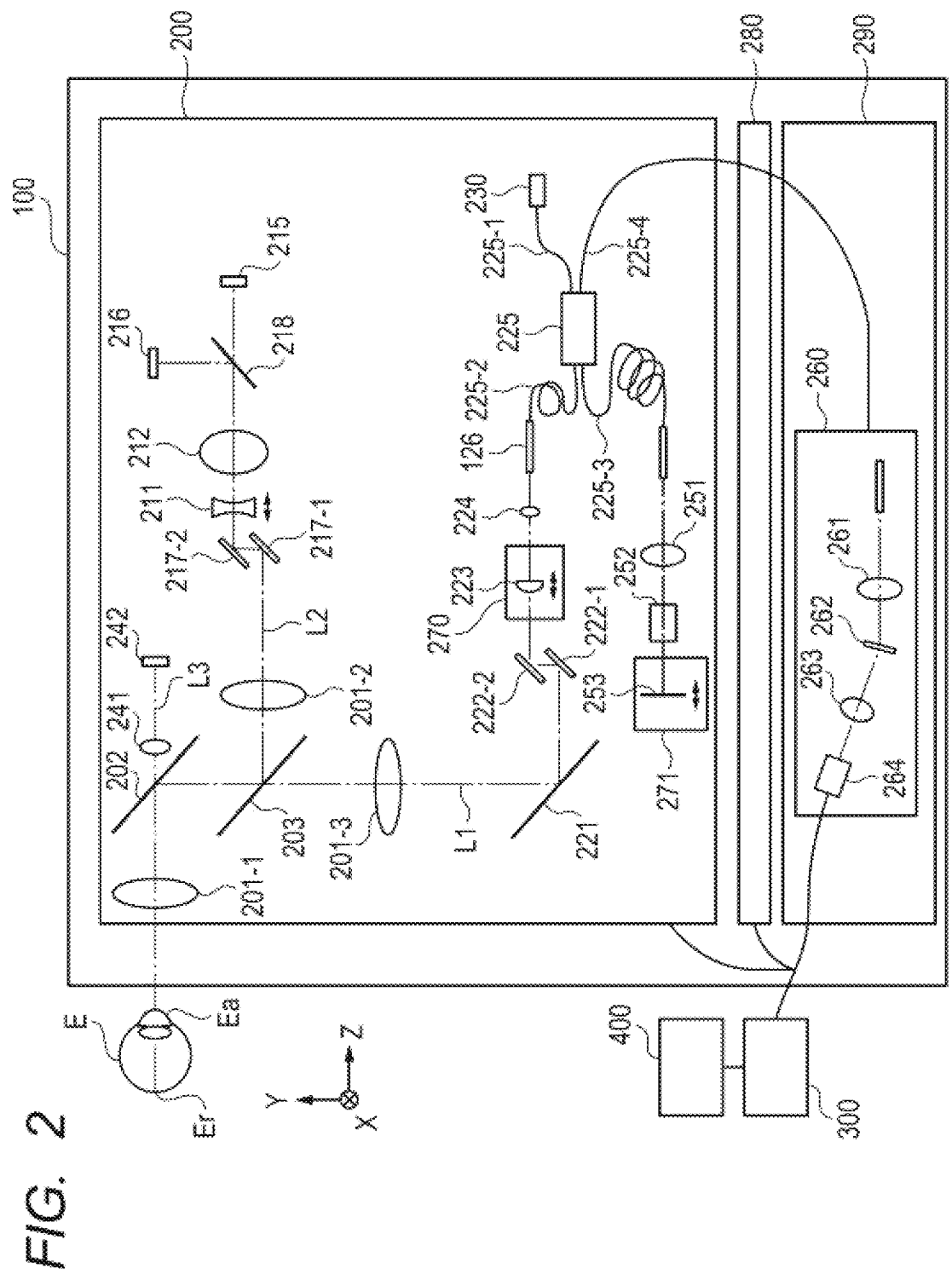
FIG. 2 is a diagram for illustrating a schematic configuration of an imaging apparatus portion of the first embodiment.
Figure 3:
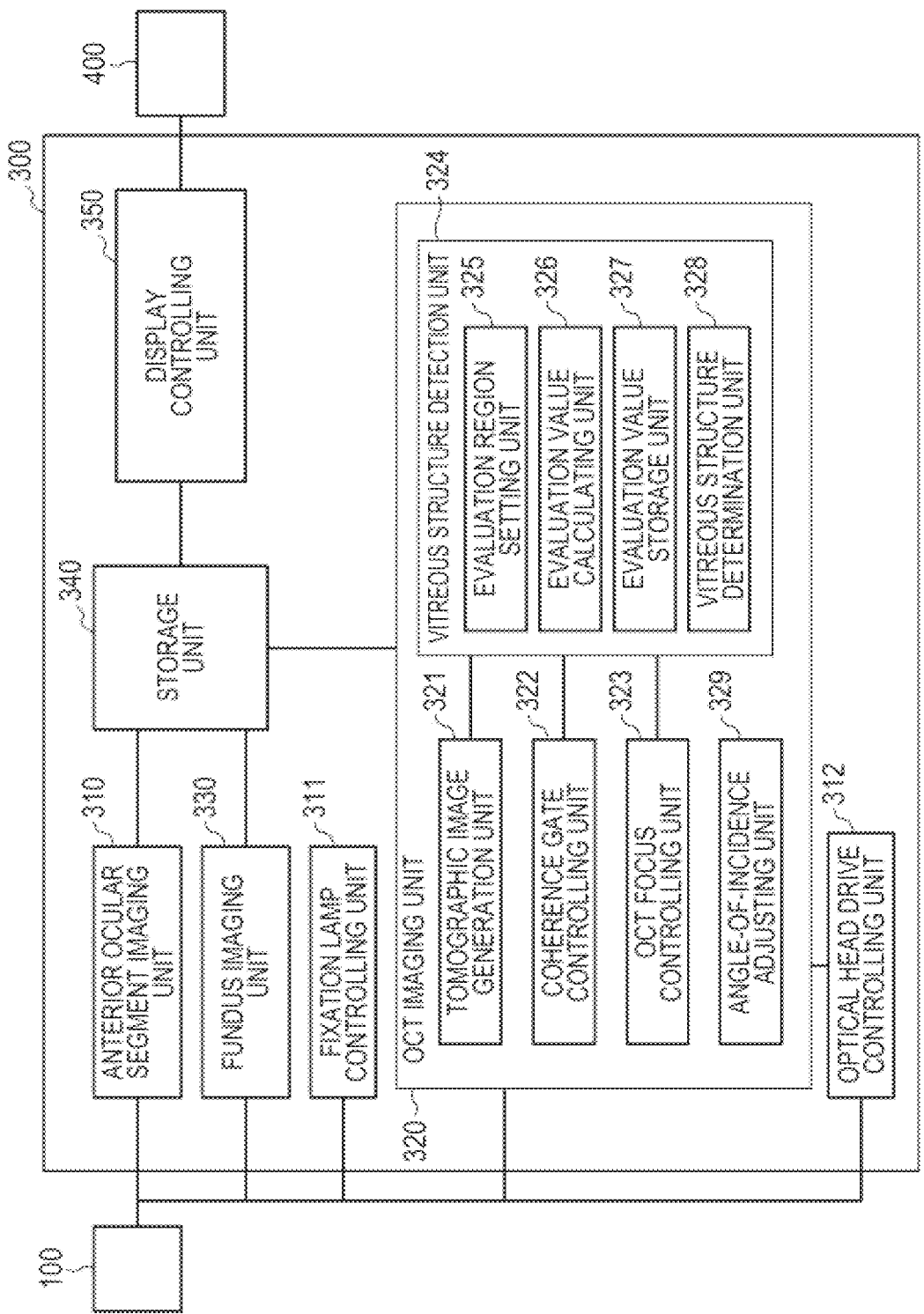
FIG. 3 is a diagram for illustrating a schematic configuration of a control portion of the first embodiment.

First referring to FIG. 1 to FIG. 3, a schematic configuration of the OCT apparatus 10 is described. The OCT apparatus 10 is configured to acquire tomographic information of an eye to be examined based on interference light obtained by causing interference between return light from the eye to be examined, which is irradiated with measurement light via an OCT scanning device, and reference light corresponding to the measurement light. The OCT apparatus 10 is capable of generating a tomographic image of a part to be imaged of the eye to be examined based on the acquired tomographic information.

The OCT apparatus 10 according to the first embodiment includes an imaging apparatus portion 100, a control portion 300 (acquisition unit), and a display portion 400. The imaging apparatus portion 100 forms an optical system configured to image the eye to be examined. The control portion 300 is configured to control the imaging apparatus portion 100 and the display portion 400. The display portion 400 is configured to display various images output by the control portion 300, information on the eye to be examined, and other information. Now, a configuration of the imaging apparatus portion 100, a configuration of the control portion 300, and a configuration of the display portion 400 are described in turn.

Configuration of Imaging Apparatus Portion 100

In FIG. 1, a schematic configuration of the OCT apparatus 10 is illustrated. As illustrated in FIG. 1, the imaging apparatus portion 100 includes an optical head 200, an electric stage 280, and a base portion 290. The optical head 200 includes a measurement optical system, which is configured to take a two-dimensional image and a tomographic image of an anterior ocular segment Ea and a fundus Er of an eye E to be examined. The electric stage 280 is capable of moving the optical head 200 in up, down, left, right, front, and back directions, and of performing alignment of the optical head 200 with respect to the eye E to be examined. The base portion 290 is connected to the electric stage 280, and the base portion 290 includes a spectroscope, which receives the interference light generated in the optical head 200.

Next, the configuration of the imaging apparatus portion 100 is described with reference to FIG. 2. In FIG. 2, a schematic configuration inside the imaging apparatus portion 100 is illustrated. In the optical head 200 of the imaging apparatus portion 100, an objective lens 201-1 is provided to face the eye E to be examined such that, when aligned with respect to the eye E to be examined using the electric stage 280, the objective lens 201-1 has an object focal point positioned at a pupil of the eye to be examined.

Further, a first dichroic mirror 202 is provided on an optical axis behind the objective lens 201-1, and a second dichroic mirror 203 is provided in a reflection direction of the first dichroic mirror 202. The first dichroic mirror 202 and the second dichroic mirror 203 each bifurcate an optical path of light from the eye E to be examined at a predetermined wavelength band into an optical path L1 of the measurement light of an OCT optical system, an optical path L2 for fundus observation and for a fixation lamp, and an optical path L3 for anterior ocular segment observation.

In the optical head 200, the first dichroic mirror 202 splits the light from the eye E to be examined into light traveling to the optical path L3, which is provided in a transmission direction of the first dichroic mirror 202, and light traveling to the optical paths L1 and L2, which are provided in the reflection direction of the first dichroic mirror 202. Moreover, the second dichroic mirror 203 splits the light from the first dichroic mirror 202 into light traveling to the optical path L1, which is provided in a transmission direction of the second dichroic mirror 203, and light traveling to the optical path L2, which is provided in a reflection direction of the second dichroic mirror 203. Positions at which the respective optical paths are provided may be suitably selected such that the optical path L3 may be provided in the reflection direction of the first dichroic mirror 202, and the optical paths L1 and L2 may be provided in the transmission direction of the first dichroic mirror 202, for example. Moreover, the optical path L1 may be provided in the reflection direction of the second dichroic mirror 203, and the optical path L2 may be provided in the transmission direction of the second dichroic mirror 203.

On the optical path L2, a lens 201-2, an X scanner 217-1, a Y scanner 217-2, lenses 211 and 212, and a third dichroic mirror 218 are provided in the stated order from the second dichroic mirror 203. Moreover, an avalanche photodiode (APD) 215 is provided in a transmission direction of the third dichroic mirror 218, and a fixation lamp 216 is provided in a reflection direction of the third dichroic mirror 218. Light traveling along the optical path L2 is split at a predetermined wavelength band by the third dichroic mirror 218, and proceeds to the optical path for fundus observation, on which the APD 215 is provided, and to the optical path for the fixation lamp, on which the fixation lamp 216 is provided. The APD 215 may be provided in the reflection direction of the third dichroic mirror 218, and the fixation lamp 216 may be provided in the transmission direction of the third dichroic mirror 218.

The APD 215 is sensitive to a wavelength of illumination light (not shown) for fundus observation, specifically, around 780 nm, and is used for observation of the eye E to be examined with the light having the wavelength. Meanwhile, the fixation lamp 216 generates visible light, and is used to form a fixation lamp configured to facilitate fixation of the eye E to be examined.

The lens 211 may be driven in directions indicated by the arrow in FIG. 2 along an optical axis direction of the optical path L2 by a motor and a drive mechanism (both not shown), which are controlled by the control portion 300, and is used to adjust focus for the fixation lamp and fundus observation.

The X scanner 217-1 (for main scanning direction) and the Y scanner 217-2 (for sub-scanning direction crossing the main scanning direction) are controlled by the control portion 300. The X scanner 217-1 and the Y scanner 217-2 are used to scan the illumination light for fundus observation and light of the fixation lamp over the fundus Er of the eye E to be examined in a suitable scanning pattern. Therefore, the X scanner 217-1 and the Y scanner 217-2 form a scanning portion configured to scan the illumination light for fundus observation. Here, optical members arranged on the optical path L2 that leads to the APD 215 form a fundus observation system. The fixation lamp 216 is connected to the control portion 300, and is controlled by the control portion 300. The control portion 300 may cause the fixation lamp 216 to flash at appropriate times in synchronization with the scanning by the X scanner 217-1 and the Y scanner 217-2, to thereby present a desired fixation lamp to the eye E to be examined.

Moreover, the optical system formed via the X scanner 217-1 and the Y scanner 217-2 also serves as an optical system configured to guide, to the APD 215, light that has returned after being scattered and reflected by the fundus Er. The APD 215 is connected to the control portion 300, and the control portion 300 may generate a fundus observation image based on an output from the APD 215, and on scanning signals of the X scanner 217-1 and the Y scanner 217-2.

On the optical path L3, a lens 241, and a charge-coupled device (CCD) 242, which is sensitive to infrared ray for anterior ocular segment observation, which is emitted from a light source (not shown), specifically, light having a wavelength of around 970 nm, are arranged. The light source (not shown), the lens 241, and the CCD 242 form an anterior ocular segment observation system configured to perform the alignment of the optical head 200 with respect to the eye E to be examined.

The optical path L1 is an optical path along which the measurement light travels in the OCT optical system, and is used to obtain an interference signal for forming a tomographic image of the fundus Er and the vitreous structure of the eye E to be examined. On the optical path L1, a lens 201-3, a mirror 221, an X scanner 222-1, a Y scanner 222-2, lenses 223 and 224, and a rod lens 126, which is provided at one end of an optical fiber 225-2, are provided in the stated order from the second dichroic mirror 203.

The X scanner 222-1 and the Y scanner 222-2 form the OCT scanning device configured to scan the measurement light over the fundus Er of the eye E to be examined in a suitable scanning pattern. The X scanner 222-1 and the Y scanner 222-2 are arranged such that the vicinity of a center position thereof is at a focus position of the lens 201-3. Therefore, when the optical head 200 is aligned with respect to the eye E to be examined, the vicinity of the center position of the scanners and a pupil position of the eye E to be examined are optically conjugate to each other.

The X scanner 217-1 and the Y scanner 217-2 described above, which are arranged on the optical path L2, are also arranged such that the vicinity of a center position thereof is at a focus position of the lens 201-2. Therefore, at the same time as the vicinity of the center position of the X scanner 222-1 and the Y scanner 222-2 is optically conjugate to the pupil position of the eye E to be examined, the vicinity of the center position of the X scanner 217-1 and the Y scanner 217-2 also has a similar conjugate relationship. With this configuration, the optical paths with object points of the scanning portion of the fundus observation system and the OCT scanning device are substantially parallel to each other between the objective lens 201-1 and the lens 201-2, and between the objective lens 201-1 and the lens 201-3. Therefore, even when scanning is performed by the X scanners 217-1 and 222-1 and the Y scanners 217-2 and 222-2, angles of incidence on the first dichroic mirror 202 and the second dichroic mirror 203 are substantially constant, with the result that a state of appropriate wavelength separation can be maintained. In FIG. 2, the optical path between the X scanner 217-1 and the Y scanner 217-2, and the optical path of the X scanner 222-1 and the Y scanner 222-2 are formed in the sheet plane, but are actually formed in a direction perpendicular to the sheet plane. It should be noted, however, that those configurations may be formed in any direction using a suitable mirror or other element.

The lens 223 may be driven and moved in directions indicated by the arrow in FIG. 2 along an optical axis of the optical path L1 by a motor 270 and a drive mechanism, which are controlled by the control portion 300, and is used for adjustment of OCT focus of the measurement light. Therefore, the lens 223 forms a focus lens configured to adjust the in-focus position of the measurement light.

Next, configurations of the optical path from an OCT light source 230, a reference optical system, and a spectroscope 260 are described. The OCT light source 230 is a light source configured to emit light used for OCT, and is connected to an optical coupler 225 via an optical fiber 225-1. In the first embodiment, as the OCT light source 230, a super luminescent diode (SLD), which is a representative low-coherent light source, and which is a light source having a center wavelength of 855 nm and a wavelength bandwidth of about 100 nm, is used. Here, the wavelength bandwidth affects a resolution in an optical axis direction of the tomographic image obtained by the OCT apparatus 10, and hence is an important parameter. Moreover, the center wavelength affects a resolution in a traverse direction of the tomographic image obtained by the OCT apparatus 10, and hence is desirably as short as possible. Therefore, in the OCT apparatus 10 according to the first embodiment, the light source having the center wavelength of 855 nm is used. Specific numerical values of the center wavelength and the wavelength bandwidth of the OCT light source 230 in this specification are merely exemplary, and other numerical values may be used instead. Moreover, the type of the light source is not limited to the SLD, and another low-coherent light source may be used instead.

The light emitted from the OCT light source 230 enters the optical coupler 225 through the optical fiber 225-1, and is split into the measurement light on the optical fiber 225-2 side and the reference light on an optical fiber 225-3 side via the optical coupler 225.

The measurement light is emitted from the rod lens 126, which is coupled to the optical fiber 225-2 connected to the optical coupler 225. Therefore, an emitting end of the rod lens 126 substantially serves as a light source of an optical system (measurement optical system) of the measurement light, and is kept in the optical conjugate relationship with the fundus Er or the vitreous structure of the eye E to be examined. Focus adjustment of the measurement light by the lens 223 is performed such that light emitted from the OCT light source 230 forms an image on the fundus Er or the vitreous structure. The measurement light is used to irradiate the fundus Er or the vitreous structure of the eye E to be examined, which is an observation target, via the optical path of the OCT optical system described above, and is reflected or scattered by the retina or the vitreous structure to reach, as the return light, the optical coupler 225 via the same optical path.

Meanwhile, the reference light enters the reference optical system through the optical fiber 225-3, which is connected to the optical coupler 225. The reference optical system includes the optical fiber 225-3, a lens 251, a dispersion compensation glass 252, and a mirror 253. The reference light is emitted from the optical fiber 225-3, passes through the lens 251, and reaches the mirror 253 via the dispersion compensation glass 252, which is inserted to match dispersion of the measurement light and the reference light, to be reflected. The reference light then returns on the same optical path to reach the optical coupler 225.

The return light from the eye E to be examined of the measurement light and the reference light reflected by the mirror 253 are combined in the optical coupler 225 to become the interference light. Here, interference occurs when an optical path length of the measurement light and an optical path length of the reference light are substantially the same. The mirror 253 is held so as to be adjustable in position in directions indicated by the arrow in FIG. 2 along an optical axis direction of the reference light by a motor 271 and a drive mechanism, which are controlled by the control portion 300. The position of the mirror 253 may be adjusted to adjust the coherence gate position, which is a position at which the optical path lengths of the measurement light and the reference light are equal to each other. As described above, the optical coupler 225 may form an optical splitter configured to split the light from the OCT light source 230 into the measurement light and the reference light, and form an interference device configured to combine the return light of the measurement light and the reference light to generate the interference light.

The interference light generated in the optical coupler 225 is guided to the spectroscope 260 (light detector), which is provided in the base portion 290, via an optical fiber 225-4. The spectroscope 260 includes a lens 261, a diffraction grating 262, a lens 263, and a line sensor 264. The interference light emitted from the optical fiber 225-4 becomes substantially parallel light via the lens 261, is dispersed for each wavelength in the diffraction grating 262, and is caused to form an image on the line sensor 264 by the lens 263. The line sensor 264 detects the interference light that has been separated by wavelength, and generates and outputs an interference signal based on the detected interference light. The line sensor 264 is connected to the control portion 300, and the control portion 300 may acquire tomographic information of the eye E to be examined based on the output from the line sensor 264, and generate the tomographic image of the eye E to be examined.

Thus, in the imaging apparatus portion 100, the OCT light source 230, the optical coupler 225, the optical fibers 225-1 to 225-4, the lens 251, the dispersion compensation glass 252, the mirror 253, and the spectroscope 260 form a Michelson interferometer. In the first embodiment, as each of the optical fibers 225-1 to 225-4, a single-mode optical fiber connected to and integrated with the optical coupler 225 is used.

Moreover, the imaging apparatus portion 100 includes the electric stage 280, which is formed of three motors (not shown) controlled by the control portion 300. The electric stage 280 may move the optical head 200 with respect to the eye E to be examined in three-dimensional (X, Y, and Z) directions, and the electric stage 280 may be controlled by the control portion 300 to perform the alignment of the optical head 200 with respect to the eye E to be examined.

Configuration of Control Portion 300

Next, the control portion 300 is described with reference to FIG. 3. FIG. 3 is a block diagram of the control portion 300. The control portion 300 includes an anterior ocular segment imaging unit 310, a fundus imaging unit 330, a fixation lamp controlling unit 311, an OCT imaging unit 320, an optical head drive controlling unit 312, a storage unit 340, and a display controlling unit 350.

The anterior ocular segment imaging unit 310 is connected to and controls a light source (not shown) for the anterior ocular segment, and the CCD 242. The anterior ocular segment imaging unit 310 may take an observation image of the anterior ocular segment Ea of the eye E to be examined based on an output from the CCD 242.

The fundus imaging unit 330 is connected to and controls an illumination light source (not shown) for fundus observation, a focus adjusting motor (not shown) for fundus observation, the X scanner 217-1, the Y scanner 217-2, and the APD 215. The fundus imaging unit 330 may take an observation image of the fundus Er of the eye E to be examined based on an output from the APD 215.

The fixation lamp controlling unit 311 is connected to the fixation lamp 216, and is capable of controlling the fixation lamp 216 to generate the visible light.

The OCT imaging unit 320 is connected to the OCT light source 230, the motor 270 configured to adjust the OCT focus position, the motor 271 configured to adjust the coherence gate position, the X scanner 222-1, the Y scanner 222-2, and the line sensor 264 of the spectroscope 260. The OCT imaging unit 320 controls those components. The OCT imaging unit 320 includes a tomographic image generation unit 321, a coherence gate controlling unit 322, an OCT focus controlling unit 323, a vitreous structure detection unit 324, and an angle-of-incidence adjusting unit 329.

The tomographic image generation unit 321 may acquire the interference signal based on the interference light that has been decomposed in wavelength by the spectroscope 260, and generate the tomographic image of the eye E to be examined based on the interference signal. As a method of generating the tomographic image based on the interference signal, any previously known method may be used.

The coherence gate controlling unit 322 (optical path length difference controlling unit) is connected to the motor 271 and a drive mechanism, and is capable of controlling the motor 271 and the drive mechanism to move the mirror 253 and hence change the optical path length of the reference light, to thereby change the difference in optical path length between the measurement light and the reference light. As a result, the coherence gate controlling unit 322 may move the coherence gate position.

The OCT focus controlling unit 323 (in-focus position controlling unit) is connected to the motor 270 and the drive mechanism, and is capable of controlling the motor 270 and the drive mechanism to move the lens 223, to thereby change the in-focus position of the measurement light.

The vitreous structure detection unit 324 is configured to detect the vitreous structure from the tomographic image generated by the tomographic image generation unit 321. The vitreous structure detection unit 324 includes an evaluation region setting unit 325, an evaluation value calculating unit 326 (calculating unit), an evaluation value storage unit 327, and a vitreous structure determination unit 328.

The evaluation region setting unit 325 is configured to determine an evaluation region corresponding to a vitreous region based on the acquired tomographic image, and set the evaluation region, from which an evaluation value is calculated in detecting the vitreous body. The evaluation value calculating unit 326 is configured to calculate the evaluation value based on a luminance value or another value in the evaluation region set by the evaluation region setting unit 325. The evaluation value storage unit 327 is configured to store the evaluation value calculated by the evaluation value calculating unit 326. The vitreous structure determination unit 328 is configured to compare the evaluation value stored in the evaluation value storage unit 327 to a predetermined threshold value, and determine that the vitreous structure is detected when the evaluation value is the threshold value or more.

The angle-of-incidence adjusting unit 329 may cause the optical head drive controlling unit 312 to control the electric stage 280 such that the optical head 200 is moved with respect to the eye E to be examined, to thereby adjust an angle of incidence of the measurement light on the fundus Er of the eye E to be examined.

The optical head drive controlling unit 312 is connected to the electric stage 280 in the optical head 200, and is capable of controlling the electric stage 280 to drive the optical head 200 three-dimensionally with respect to the eye E to be examined.

The storage unit 340 is configured to store information on a subject to be examined, an anterior ocular segment observation image generated by the anterior ocular segment imaging unit 310, a fundus observation image generated by the fundus imaging unit 330, the tomographic image generated by the OCT imaging unit 320, and other data.

The display controlling unit 350 is connected to the display portion 400, and is capable of displaying, on the display portion 400, the information on the subject to be examined, various images, and other data stored in the storage unit 340.

The control portion 300 may be formed using a general computer. Moreover, the control portion 300 may be designed as a computer specific to the OCT apparatus 10. In the first embodiment, the control portion 300 is formed separately from the imaging apparatus portion 100 and the display portion 400, but may be formed integrally therewith. Further, components of the control portion 300 described above may be formed of modules executed by a central processing unit (CPU), a micro-processing unit (MPU), or another arithmetic unit of the control portion 300, or may be formed of application specific integrated circuits (ASICs) and other circuits providing particular functions. The storage unit 340 and the evaluation value storage unit 327 may be formed using any storage media, for example, optical discs and memories.

Display Portion 400

The display portion 400 is connected to the control portion 300, and is capable of displaying information on the subject to be examined (patient), various images, and other data, which are stored in the storage unit 340, based on an output from the display controlling unit 350 of the control portion 300. The display portion 400 may be formed using any monitor. In the first embodiment, the display portion 400 is formed separately from the imaging apparatus portion 100 and the control portion 300, but may be formed integrally therewith.

Imaging Sequence for Vitreous Body

Figure 4:
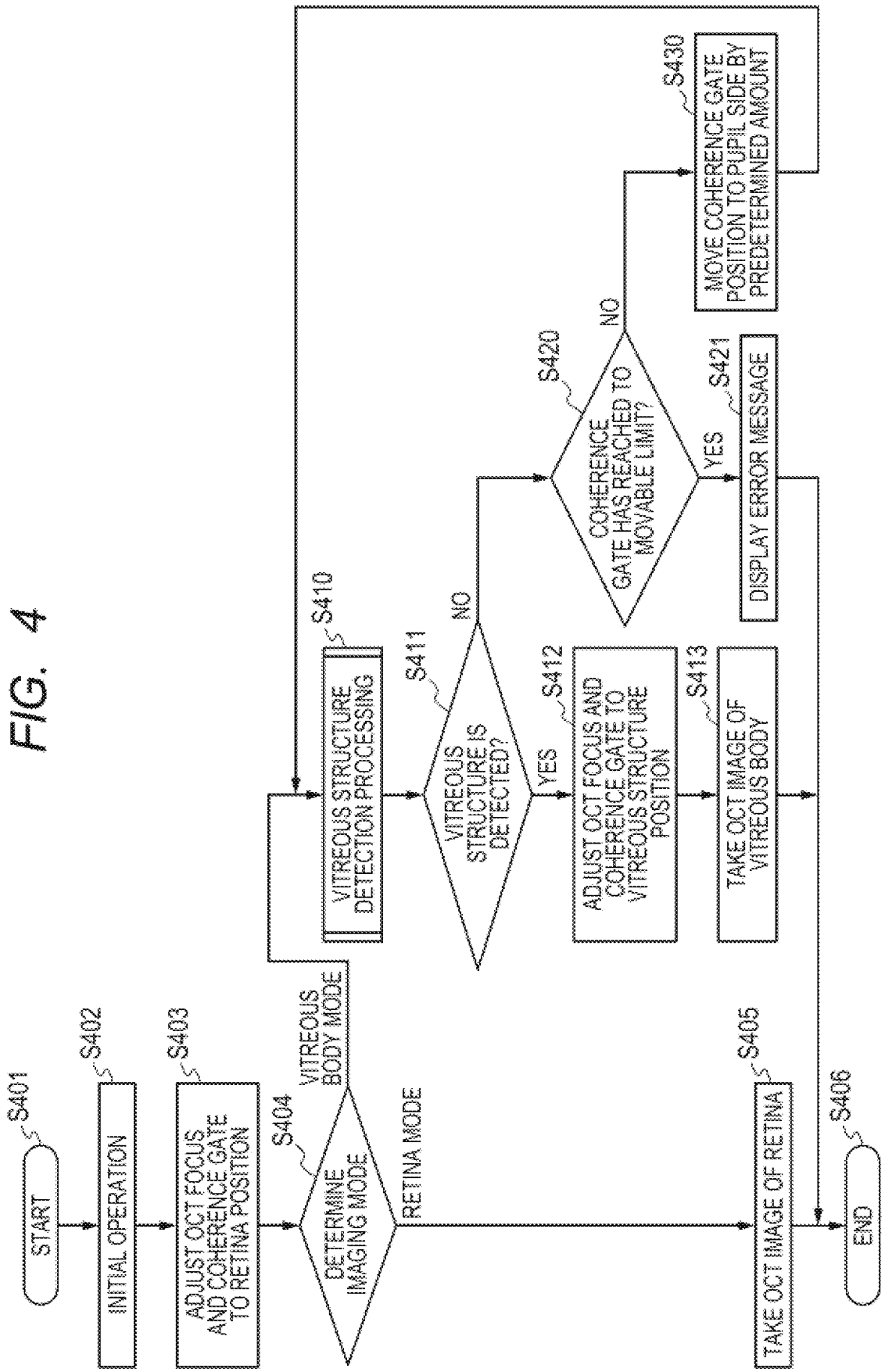
FIG. 4 is a flow chart for illustrating an imaging sequence of the first embodiment.

Now, an imaging sequence for the vitreous body (vitreous structure) is described with reference to FIG. 4 to FIG. 6D. FIG. 4 is a flow chart for illustrating the imaging sequence for the vitreous structure according to the first embodiment. In FIG. 5A to FIG. 5D, examples of a display content of the display portion 400 are illustrated. In FIG. 6A to FIG. 6D, examples of the acquired tomographic image are illustrated.

Figure 5B:
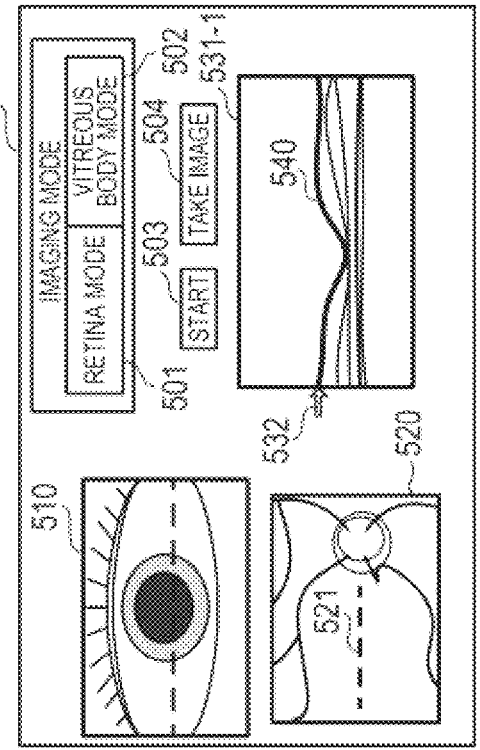
FIG. 5B is a diagram for illustrating another example of the display content of the display portion of the first embodiment.
Figure 5D:
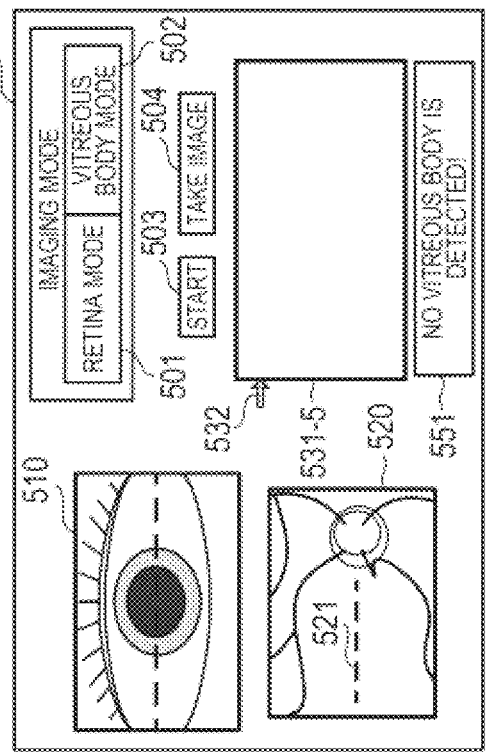
FIG. 5D is a diagram for illustrating yet another example of the display content of the display portion of the first embodiment.
Figure 5A:
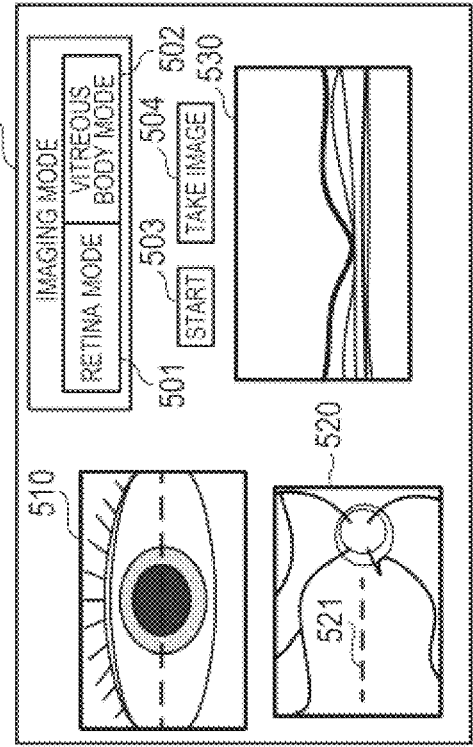
FIG. 5A is a diagram for illustrating an example of a display content of a display portion of the first embodiment.
Figure 5C:
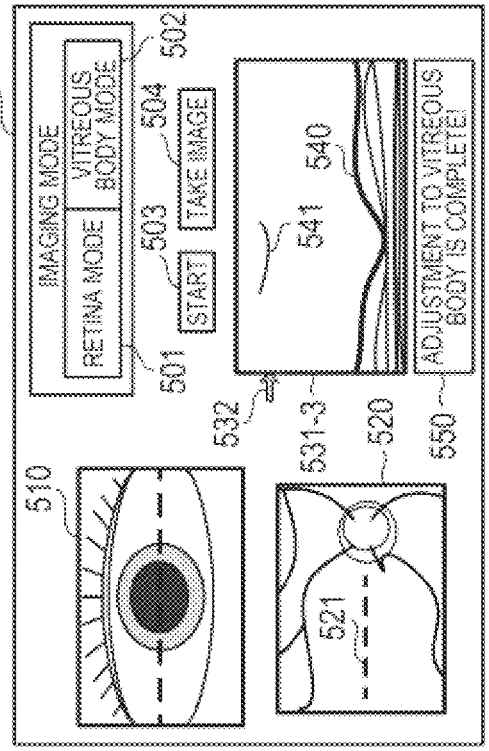
FIG. 5C is a diagram for illustrating still another example of the display content of the display portion of the first embodiment.

First, in Step S401 of FIG. 4, the display controlling unit 350 detects that a start button 503 of a screen 500, which is illustrated in FIG. 5A, has been pressed, and starts imaging.

In Step S402, the OCT apparatus 10 performs an initial operation in taking the tomographic image. In the initial operation, the anterior ocular segment imaging unit 310 takes an anterior ocular segment observation image 510 based on an output signal from the CCD 242. Then, the optical head drive controlling unit 312 performs an alignment operation in X, Y, and Z directions of the optical head 200 with respect to the eye E to be examined based on the anterior ocular segment observation image 510. The alignment of the optical head 200 with respect to the eye E to be examined may be performed by an examiner operating the electric stage 280 based on the anterior ocular segment observation image 510 displayed on the display portion 400. Then, the fundus imaging unit 330 takes a fundus observation image 520 based on an output signal from the APD 215, and performs focus adjustment of the fundus observation image 520.

Thereafter, the OCT imaging unit 320 takes the tomographic image based on an output signal from the line sensor 264. At the same time, the display controlling unit 350 displays the anterior ocular segment observation image 510, the fundus observation image 520, and a tomographic image 530 on the screen 500 illustrated in FIG. 5A. Here, the tomographic image 530 is a tomographic image at a position of a broken line 521 illustrated in the fundus observation image 520.

In Step S403, the OCT focus controlling unit 323 adjusts the OCT focus position for the tomographic image 530 to the vicinity of the retina using focus information of the fundus observation image 520. Moreover, the coherence gate controlling unit 322 adjusts the coherence gate position so that the retina can be observed on the tomographic image 530 using information of the tomographic image 530. Here, the adjustment of the coherence gate position may be performed by any method. For example, the coherence gate position may be adjusted such that a portion corresponding to the retina in the tomographic image 530 is displayed at a particular position in the tomographic image 530. Moreover, the coherence gate position may be adjusted by being moved by a predetermined amount from the coherence gate position at which the luminance value of the tomographic image 530 is largest.

Figure 6A:
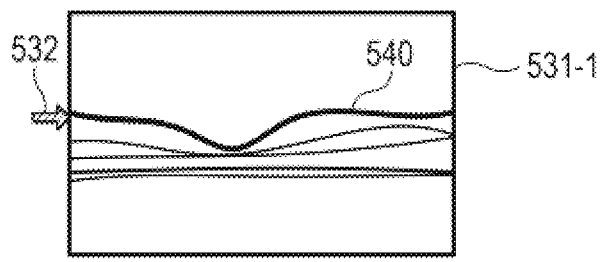
FIG. 6A is a diagram for illustrating an example of an acquired tomographic image of the first embodiment.
Figure 6B:
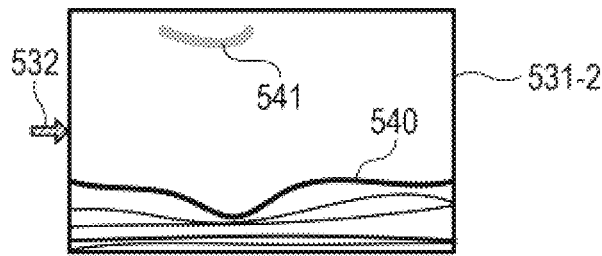
FIG. 6B is a diagram for illustrating another example of the acquired tomographic image of the first embodiment.
Figure 6C:
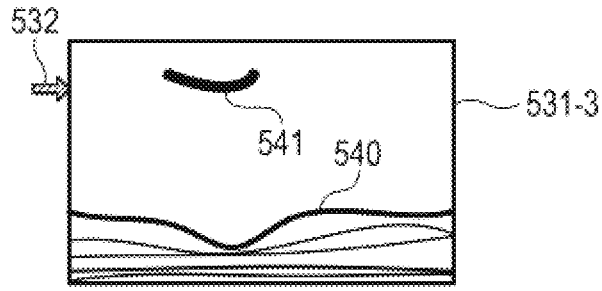
FIG. 6C is a diagram for illustrating still another example of the acquired tomographic image of the first embodiment.
Figure 6D:
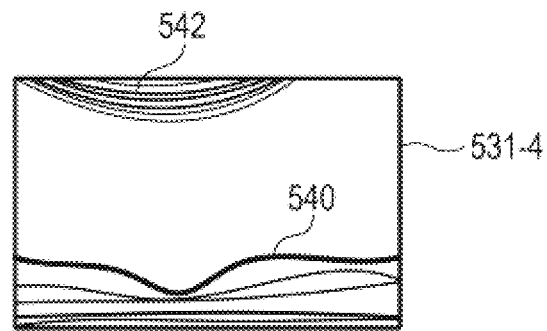
FIG. 6D is a diagram for illustrating yet another example of the acquired tomographic image of the first embodiment.

Then, as illustrated in a tomographic image 531-1 of FIG. 5B and FIG. 6A, the tomographic image generation unit 321 generates a tomographic image in a state in which the OCT focus position is in the vicinity of the retina, and in which a coherence gate is adjusted so that the retina can be observed in the tomographic image. Here, a tomographic image 540 of the retina is shown in the tomographic image 531-1, and an arrow 532 indicates a position in the depth direction at the OCT focus in the tomographic image. Here, the OCT focus controlling unit 323 adjusts the OCT focus position using the focus information of the fundus observation image, but adjustment may be performed such that the retina is at OCT focus using the information of the tomographic image.

In Step S404, operation is switched depending on the imaging mode. When the display controlling unit 350 determines that a retina mode 501 is selected on the screen 500, the processing proceeds to Step S405.

In Step S405, the display controlling unit 350 detects that a "take image" button 504 on the screen 500 has been pressed, and takes the tomographic image under a state in which the coherence gate position and the OCT focus position have been adjusted to image the retina. Then, in Step S406, the storage unit 340 stores the tomographic image, and the processing of taking the tomographic image (OCT image) of the retina is ended.

Meanwhile, in Step S404, when the display controlling unit 350 determines that a vitreous body mode 502 is selected on the screen 500, the processing proceeds to Step S410.

In Step S410, the vitreous structure detection unit 324 of the OCT imaging unit 320 performs vitreous structure detection processing. In the vitreous structure detection processing, the OCT imaging unit 320 moves the OCT focus position to a pupil side (vitreous body side), and starts an operation of searching for the vitreous structure. The details are described in a sequence of the vitreous structure detection processing, which is to be described later.

In Step S411, the vitreous structure determination unit 328 of the vitreous structure detection unit 324 determines whether the vitreous structure has been detected in Step S410. The position at which the vitreous structure is detected with respect to the retina varies among individuals due to the posterior vitreous detachment and other causes. Therefore, under the state in which the coherence gate position is adjusted to the retina position of the fundus Er, there are cases in which no vitreous structure is detected. When it is determined in step S411 that no vitreous structure is detected, the processing proceeds to Step S420.

In Step S420, the coherence gate controlling unit 322 determines whether the coherence gate position has reached a limit of its movable position, and when the coherence gate position has not reached the limit, the processing proceeds to Step S430.

In Step S430, the coherence gate controlling unit 322 moves the mirror 253 by the predetermined amount to move the coherence gate position to the pupil side by the predetermined amount, to thereby move a position at which the tomographic image is taken further to the pupil side in the depth direction. As a result, as shown in a tomographic image 531-2 of FIG. 6B, a tomographic image in which the retina has been moved downward in the image, in other words, an imaging position has been moved to a shallower direction, is taken. Here, a vitreous structure 541 is shown in the tomographic image 531-2. When the coherence gate position is moved in Step S430, the processing returns to Step S410. In Step S410, the vitreous structure detection unit 324 starts the vitreous structure detection processing again using the tomographic image 531-2 that has been taken with the moved coherence gate position.

When it is determined in Step S411 that the vitreous structure detection unit 324 has detected the vitreous structure, the processing proceeds to Step S412.

In step S412, the OCT focus controlling unit 323 and the coherence gate controlling unit 322 adjust the OCT focus position and the coherence gate position so as to image the vicinity of the position at which the vitreous structure is present based on positional information of the detected vitreous structure. At this time, the coherence gate position may be adjusted such that the vitreous structure is substantially at the center of the tomographic image in the depth direction, or may be adjusted to a position at which the vitreous structure can be observed simultaneously with the retina. Through the processing of Step S412, as shown in a tomographic image 531-3 of FIG. 5C and FIG. 6C, the OCT focus position and the coherence gate position are adjusted to a state in which the vitreous structure can be imaged appropriately. Moreover, when the adjustments are complete, the display controlling unit 350 displays a status message 550 of FIG. 5C to provide a notice of the completion of the adjustments to a user.

In Step S413, the display controlling unit 350 detects that the "take image" button 504 on the screen 500 has been pressed, and the OCT imaging unit 320 takes the tomographic image under the state in which the adjustments have been made so that the vitreous structure can be imaged appropriately. Then, in Step S406, the storage unit 340 stores the tomographic image, and ends the processing of taking the tomographic image of the vitreous structure.

A signal of the vitreous structure is weak, and hence tends to be buried in speckle noise and other noise. Therefore, in Step S413, there may be performed processing in which the control portion 300 takes the tomographic image a plurality of times in succession, and superimposes the tomographic images on one another. As a result, as illustrated in a tomographic screen 531-4 of FIG. 6D, a clearer tomographic image of the vitreous structure 542 can be taken, and the vitreous structure can be observed more appropriately. Moreover, the control portion 300 may perform contrast control on the tomographic image, which has been taken in Step S413, such that the vitreous structure can be seen more clearly in the tomographic image.

In Step S420, when the coherence gate controlling unit 322 determines that the coherence gate position has reached the limit of its movable position, the processing proceeds to Step S421. In Step S421, the display controlling unit 350 displays an error message 551 illustrated in FIG. 5D to provide, to the user, an alarm to the effect that no vitreous structure is detected. Then, in Step S406, the processing of taking the tomographic image is ended without the storage unit 340 storing the tomographic image.

Sequence of Vitreous Structure Detection Processing

The depth of focus in OCT is shallow, and hence under the state in which the focus position is adjusted to the retina position of the fundus Er, the vitreous structure is blurred and not imaged clearly. Here, as a method of searching for the vitreous structure, while the OCT focus position is moved to the pupil side, the tomographic image is acquired at each OCT focus position, and the OCT focus position at which the evaluation value of the vitreous structure is highest is determined to be a position at which the vitreous structure is present.

Figure 7:
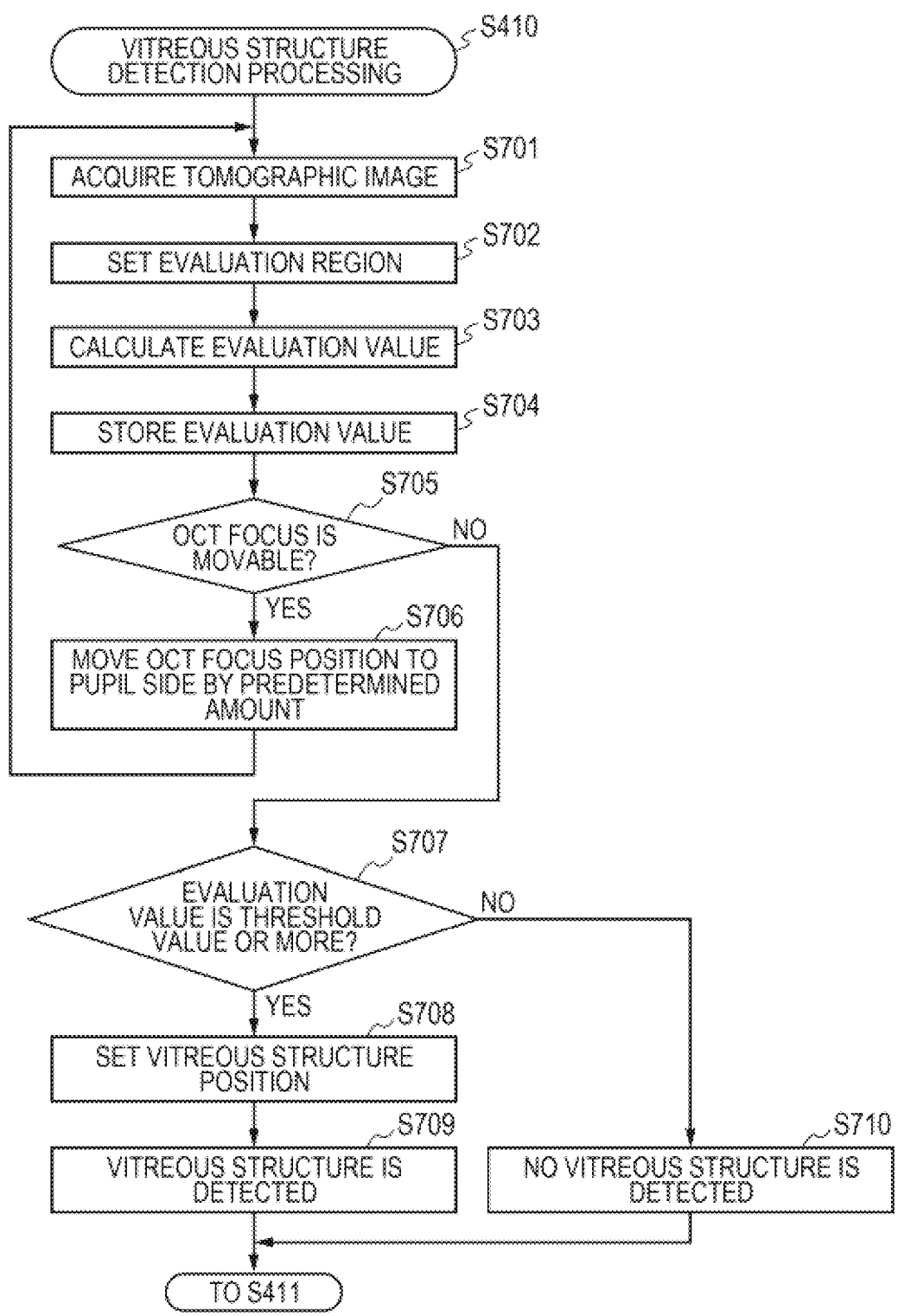
FIG. 7 is a flow chart for illustrating a sequence of vitreous structure detection processing of the first embodiment.
Figure 8A:
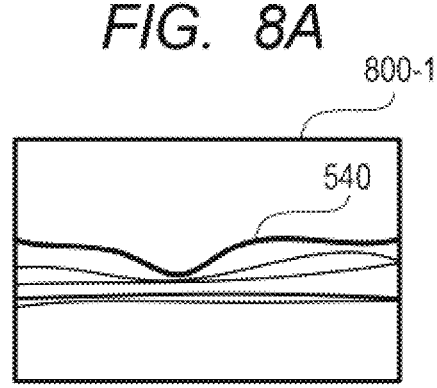
FIG. 8A is a diagram for illustrating setting of an evaluation region for a vitreous body of the first embodiment.
Figure 8B:
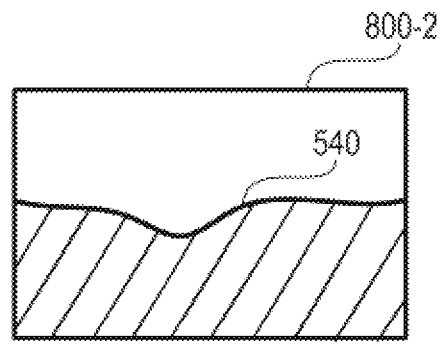
FIG. 8B is a diagram for illustrating a setting example of the evaluation region for the vitreous body of the first embodiment.
Figure 9A:
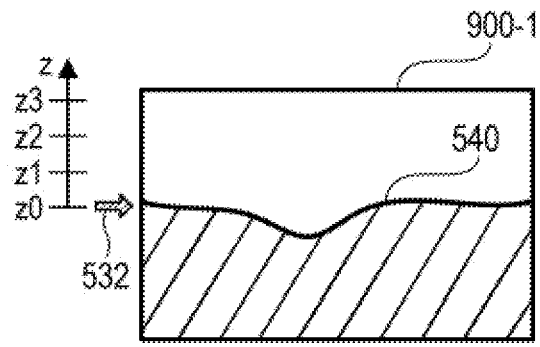
FIG. 9A is a diagram for illustrating an example of evaluation value calculation in a case where a vitreous structure is not imaged.
Figure 9B:
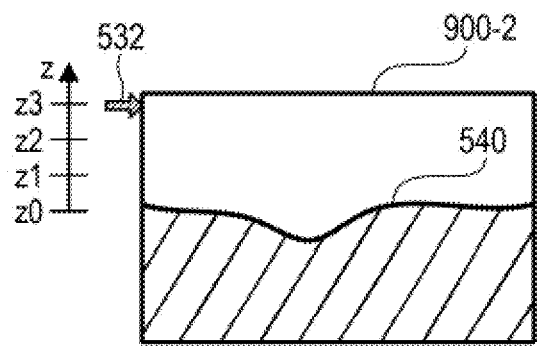
FIG. 9B is a diagram for illustrating another example of the evaluation value calculation in the case where the vitreous structure is not imaged.
Figure 9C:
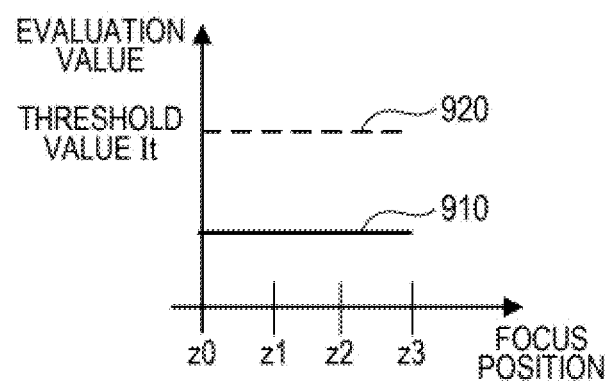
FIG. 9C is a graph for showing the examples of the evaluation value calculation in the case where the vitreous structure is not imaged.

Now, the sequence of the vitreous structure detection processing of Step S410 in the first embodiment is described with reference to FIG. 7 to FIG. 10D. FIG. 7 is a flow chart for illustrating the sequence of the vitreous structure detection processing of the first embodiment. FIG. 8A and FIG. 8B are diagrams for illustrating setting of a vitreous body evaluation region. FIG. 9A to FIG. 9C are diagrams for illustrating evaluation value calculation in a case where the vitreous structure is not imaged. FIG. 10A to FIG. 10D are diagrams for illustrating evaluation value calculation in a case where the vitreous structure is imaged.

When the vitreous structure detection processing is started in Step S410 of FIG. 4, the processing proceeds to Step S701 illustrated in FIG. 7. In Step S701, the vitreous structure detection unit 324 acquires the tomographic image generated by the tomographic image generation unit 321.

In Step S702, the evaluation region setting unit 325 sets the evaluation region in the tomographic image for use in searching for the vitreous structure. Here, with the use of luminance information of a tomographic image 800-1 illustrated in FIG. 8A, a region on the side of the retina and the choroid (shaded portion) is recognized as illustrated in FIG. 8B. Then, a region (vitreous region) other than the shaded region in a tomographic image 800-2 illustrated in FIG. 8B is set as the evaluation region. A method of recognizing the region on the side of the retina and the choroid may be any method. For example, a contrast of the tomographic image may be enhanced and luminances of the tomographic image are binarized to recognize a region corresponding to the retina and the choroid, to thereby recognize an area below the region as the region on the side of the retina and the choroid. Moreover, the luminance values in the depth direction of the tomographic image may be compared to one another to identify a peak of the luminance values corresponding to the retina position, and a direction in which many of other peaks of the luminance values further appear from the position of the peak may be recognized as the region corresponding to the retina and the choroid. Which of the upper and lower directions in the image is the choroid side may be determined based on a relationship between the position corresponding to the retina and the coherence gate position relating to an imaging position. Moreover, when the region on the side of the retina and the choroid cannot be recognized in the tomographic image, the entire image can be set as the evaluation region.

In Step S703, the evaluation value calculating unit 326 calculates an evaluation value (first evaluation value) based on the set evaluation region. Here, in the first embodiment, a total luminance of the evaluation region is used as the evaluation value, but the evaluation value is not limited thereto. For example, a sharpness of a luminance distribution, an average luminance, a maximum luminance, a contrast, an amplitude of a particular frequency component, and another evaluation value of the evaluation region may be used. In the configuration in which the amplitude of the particular frequency component is used in calculating the evaluation value, when the focus position is at the vitreous structure, the amplitude of the particular frequency component (high-frequency component) of the image becomes larger. Therefore, the amplitude may be used in calculating the evaluation value to determine whether the vitreous structure is detected.

In Step S704, the evaluation value storage unit 327 stores the calculated evaluation value in association with the OCT focus position.

In Step S705, the OCT focus controlling unit 323 determines whether the OCT focus position is movable to the pupil side (vitreous body side). Here, as an example, the OCT focus position is movable within the range of the tomographic image displayed on the screen 500. When it is determined that the OCT focus position is movable, the processing proceeds to Step S706.

In Step S706, the OCT focus controlling unit 323 moves the OCT focus position to the pupil side by a predetermined amount. Then, after the movement of the OCT focus position is complete, the processing returns to Step S701. As an example, tomographic images 900-1 and 900-2 obtained when the OCT focus position is set to positions z0 and z3 in the depth direction are illustrated in FIG. 9A and FIG. 9B, respectively, and a graph of the evaluation values obtained when the OCT focus position is moved in a range of positions z0 to z3 is shown in FIG. 9C.

When the OCT focus position has reached an upper edge of the tomographic image, and the OCT focus controlling unit 323 determines in Step S705 that the OCT focus position is not movable, the processing proceeds to Step S707.

In Step S707, in order to determine whether the vitreous structure is detected, the vitreous structure determination unit 328 compares the stored evaluation value to the predetermined threshold value, which has been acquired in advance. When the vitreous structure is not imaged in the tomographic image, at a focus position in the range of the positions z0 to z3, an evaluation value 910 is lower than a threshold value It 920 as shown in FIG. 9C. Therefore, the vitreous structure determination unit 328 determines that no vitreous structure is detected, and the processing proceeds to Step S710.

Then, in Step S710, the vitreous structure determination unit 328 determines that no vitreous structure is detected to end the vitreous structure detection processing, and in Step S411 of FIG. 4, the processing proceeds to Step S420. Thereafter, the OCT imaging unit 320 follows the processing depending on the determination in Step S420, and when the coherence gate position is movable, the OCT imaging unit 320 moves the coherence gate position to the pupil side by the predetermined amount in Step S430. Then, after the OCT imaging unit 320 completes moving the coherence gate position to the pupil side, the processing returns again to Step S410.

Figure 10A:
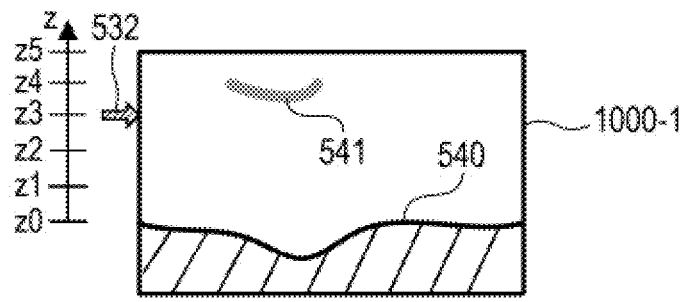
FIG. 10A is a diagram for illustrating an example of evaluation value calculation in a case where the vitreous structure is imaged.
Figure 10B:
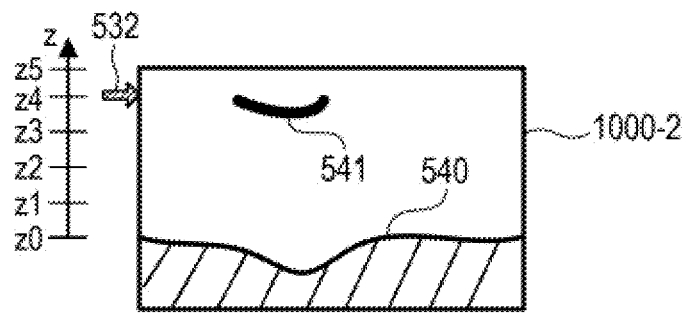
FIG. 10B is a diagram for illustrating another example of the evaluation value calculation in the case where the vitreous structure is imaged.
Figure 10C:
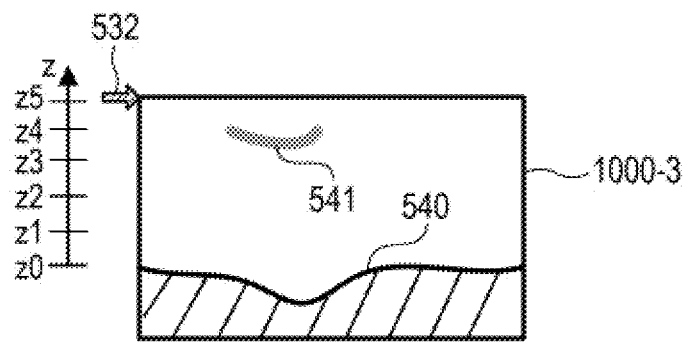
FIG. 10C is a diagram for illustrating still another example of the evaluation value calculation in the case where the vitreous structure is imaged.
Figure 10D:
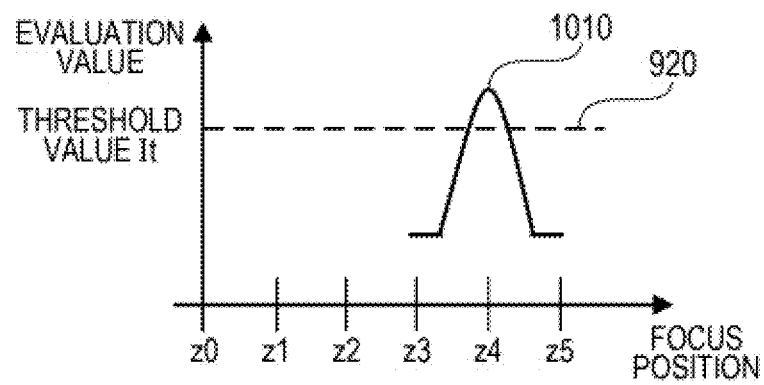
FIG. 10D is a graph for showing the examples of the evaluation value calculation in the case where the vitreous structure is imaged.

Thereafter, in Step S701, the vitreous structure detection unit 324 acquires a tomographic image in which the retina has been moved downward in the tomographic image from the tomographic image generation unit 321. Here, there is described a case in which a tomographic image in which the vitreous structure can be observed as in a tomographic image 1000-1 of FIG. 10A is acquired from the tomographic image generation unit 321. In this case, the vitreous structure detection unit 324 repeats Steps S701 to S706 again to move the OCT focus position in a range of the positions z3 to z5 in the depth direction. Tomographic images 1000-1 to 1000-3 obtained at respective positions of the OCT focus position are illustrated in FIG. 10A to FIG. 10C, respectively, and a graph of the evaluation values of the tomographic images is shown in FIG. 10D. In this example, the OCT focus is at the vitreous structure 541 in the tomographic image 1000-2 illustrated in FIG. 10B.

When the OCT focus position reaches the upper edge of the tomographic image, and the OCT focus controlling unit 323 determines in Step S705 that the OCT focus is not movable, the processing proceeds to Step S707.

In the case of FIG. 10B, the OCT focus is at the vitreous structure in the tomographic image 1000-2, and hence at the OCT focus position of the position z4, an evaluation value 1010 is the threshold value It 920 or more as shown in FIG. 10D. Therefore, in Step S707, the vitreous structure determination unit 328 determines that the vitreous structure is detected, and the processing proceeds to Step S708.

In Step S708, the vitreous structure determination unit 328 sets a vitreous structure position corresponding to the evaluation value 1010 to the position z4. Next, the vitreous structure determination unit 328 determines in Step S709 that the detection of the vitreous structure is complete to end the vitreous structure detection processing, and in Step S411 of FIG. 4, the processing proceeds to Step S412. Then, in Step S412, the OCT focus position and the coherence gate position are adjusted in accordance with the position at which the vitreous structure is present.

Here, in this sequence, after the OCT focus position is moved up to the upper edge of the range in which the tomographic image displayed on the screen 500 is taken, the stored evaluation value is compared to the threshold value, and it is determined that the vitreous structure is present based on the largest evaluation value exceeding the threshold value. In this case, of the vitreous structure within the range in which the tomographic image is taken, there can be detected a position at which a signal based on the return light from the vitreous structure of the measurement light is the strongest.

Meanwhile, after the evaluation value is calculated in Step S703, the evaluation value may be sequentially compared to the threshold value It to determine whether the vitreous structure is present. In this case, it can be determined that the vitreous structure is present as soon as the threshold value It is exceeded, and hence the vitreous structure can be detected in a shorter time, although there is a possibility of detecting an end portion of the vitreous structure.

An amount by which the coherence gate controlling unit 322 moves the coherence gate position in Step S430 may be freely selected. Foe example, the coherence gate controlling unit 322 may move the coherence gate position by an amount that is equivalent to a total amount by which the OCT focus position is moved in the vitreous structure detection processing in Step S410. Moreover, the movement amount of the coherence gate position may be restricted such that the retina does not fall out of the imaging range.

The amount by which the OCT focus controlling unit 323 moves the OCT focus position in Step S706 may be freely selected, and accuracy of adjustment becomes higher as the amount becomes smaller. However, when the movement amount is small, the number of times of evaluation of the image is large, and the detection takes time. Therefore, the movement amount by which the OCT focus position is moved may be determined in consideration of the balance between the time required for the detection and the accuracy of adjustment.

Figure 11A:
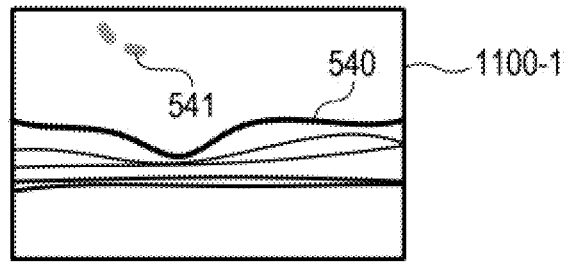
FIG. 11A is a diagram for illustrating an example of processing for facilitating detection of the vitreous structure.
Figure 11B:
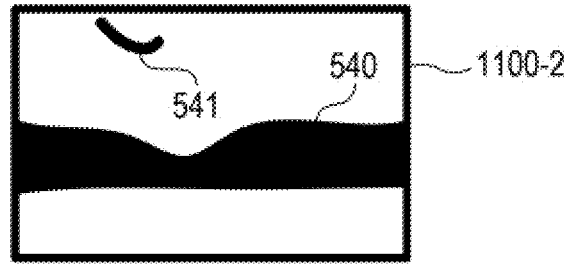
FIG. 11B is a diagram for illustrating another example of the processing for facilitating detection of the vitreous structure.
Figure 11C:
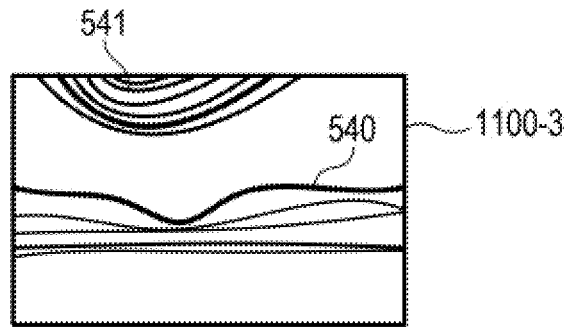
FIG. 11C is a diagram for illustrating still another example of the processing for facilitating detection of the vitreous structure.

The vitreous body is generally a clear and colorless jelly-like tissue, and hence little light is scattered and reflected thereon, with the result that a signal intensity of the vitreous structure 541 is weak as illustrated in a tomographic image 1100-1 of FIG. 11A. Therefore, in order to facilitate detection of the vitreous structure, the following processing may be additionally performed.

Contrast Control on Tomographic Image

A retina signal and a vitreous structure signal have a large difference in intensity, and hence when the contrast control is performed such that the retina is seen clearly, the vitreous body becomes difficult to see. Therefore, when detecting the vitreous structure, the vitreous structure detection unit 324 may use in calculating the evaluation value an image obtained by performing an adjustment to increase a contrast to the extent that the intensity of the retina signal is saturated as illustrated in a tomographic image 1100-2 of FIG. 11B. As a result, the intensity of the vitreous structure signal is also increased, and the vitreous structure is easily detected. In this case, the vitreous structure detection unit 324 also serves as a contrast adjusting unit.

Superimposition of Tomographic Images

As described above, the vitreous structure signal is weak, and hence is buried in speckle noise and other noise. Therefore, when detecting the vitreous structure, the vitreous structure detection unit 324 may acquire a plurality of tomographic images, and use in calculating the evaluation value a superimposed image obtained by averaging the tomographic images as illustrated in a tomographic image 1100-3 of FIG. 11C. As a result, the evaluation value can be calculated based on a tomographic image in which the speckle noise and other noise are reduced, end hence the vitreous structure is easily detected.

As described above, the OCT apparatus 10 according to the first embodiment includes the optical coupler 225 configured to generate the interference light between the return light obtained by irradiating the eye E to be examined with the measurement light obtained by splitting the light from the OCT light source 230, and the reference light obtained by splitting the light from the OCT light source 230, and the spectroscope 260 configured to detect the interference light. The OCT apparatus 10 also includes the coherence gate controlling unit 322 configured to control the motor 271 and other components, which are configured to drive the mirror 253, to control the optical path length of the reference light, to thereby control the difference in optical path length between the measurement light and the reference light. The OCT apparatus 10 further includes the OCT focus controlling unit 323 configured to control the motor 270 and other components, which are configured to drive the lens 223, to control the OCT focus position (in-focus position of the measurement light). The OCT apparatus 10 includes the control portion 300 configured to acquire the tomographic information of the eye E to be examined using the information on the interference light detected by the spectroscope 260. The OCT apparatus 10 also includes the vitreous structure detection unit 324 configured to detect the vitreous structure 541 of the eye E to be examined using the tomographic information of the eye E to be examined, which is acquired by the control portion 300.

The vitreous structure detection unit 324 is configured to detect the vitreous structure 541 of the eye E to be examined using the tomographic information of the eye E to be examined that is acquired alter at least one of the difference in optical path length and the in-focus position is controlled by at least one of the mirror 253 and the lens 223. More specifically, the tomographic information of the eye E to be examined is acquired after the lens 223 is controlled by the OCT focus controlling unit 323 to move the OCT focus position. Thereafter, the evaluation region setting unit 325 of the vitreous structure detection unit 324 determines, from the acquired tomographic information of the eye E to be examined, the information corresponding to the vitreous region of the eye E to be examined, and sets, based on the determined information, the evaluation region in the tomographic image generated based on the tomographic information. Thereafter, the evaluation value calculating unit 326 of the vitreous structure detection unit 324 calculates the evaluation value in the evaluation region using the luminance values and other information in the evaluation region. The vitreous structure determination unit 326 of the vitreous structure detection unit 324 compares the calculated evaluation value to the predetermined threshold value, and determines that the vitreous structure is detected when the evaluation value is the threshold value or more. The OCT imaging unit 320 of the control portion 300 moves the lens 223 to be in focus at the OCT focus position corresponding to the evaluation value obtained when the vitreous structure is detected, and acquires tomographic information of the vitreous structure.

The vitreous structure detection unit 324 sequentially changes the OCT focus position to search for the vitreous structure described above. Moreover, when the OCT focus position is changed by the predetermined amount by the lens 223, the coherence gate controlling unit 322 controls the mirror 253 to move the coherence gate position. At this time, the mirror 253 is controlled to change the difference in optical path length so as to obtain tomographic information of the eye E to be examined after being moved in the same direction as the direction in which the OCT focus position is changed in the depth direction of the eye E to be examined. Moreover, when the calculated evaluation value does not exceed the threshold value, the vitreous structure detection unit 324 causes the coherence gate controlling unit 322 to control the mirror 253 in accordance with the direction in which the OCT focus position is changed, to thereby move the coherence gate position. More specifically, the mirror 253 is controlled such that the difference in optical path length is changed by the predetermined amount so as to obtain tomographic information of the eye E to be examined after being moved in the same direction as the direction in which the OCT focus position is moved in the depth direction of the eye E to be examined. Thereafter, the vitreous structure detection unit 324 further changes the OCT focus position by the predetermined amount with the lens 223, and uses the acquired tomographic information of the eye E to be examined to search for the vitreous structure. The vitreous structure detection unit 324 repeatedly searches for the vitreous structure until the vitreous structure is detected.

With the OCT apparatus 10 according to the first embodiment, the above-mentioned configuration is used to search for the vitreous structure while moving the OCT focus position and the coherence gate position, to thereby detect the vitreous structure appropriately. As a result, the OCT apparatus 10 can image the vitreous structure appropriately. In the first embodiment, the OCT focus position and the coherence gate position are changed to search for the vitreous structure, but the method of searching for the vitreous structure is not limited thereto. For example, only the OCT focus position may be changed to search for the vitreous structure, or only the coherence gate position, which corresponds to the difference in optical path length between the measurement light and the reference light, may be changed to search for the vitreous structure. Also in those cases, the tomographic image may be acquired after the OCT focus position or the coherence gate position is adjusted to the position at which the vitreous structure is detected, to thereby image the vitreous structure appropriately.

In addition, in the first embodiment, the vitreous structure detection unit 324 searches for the vitreous structure using the tomographic image generated based on the tomographic information of the eye E to be examined that is acquired by the control portion 300. However, without limiting to the tomographic image, the vitreous structure detection unit 324 may search for the vitreous structure using, for example, tomographic information of the eye E to be examined, from which the tomographic image is generated, including an output signal from the spectroscope 260, and a signal obtained by performing suitable signal processing on the signal. As can be seen from the fact that the tomographic image is generated from those pieces of information, those pieces of information correspond to information (e.g., luminance values) in the tomographic image. Therefore, in this case, the evaluation region setting unit 325 may determine, of the tomographic information of the eye E to be examined, information corresponding to the vitreous region in the tomographic image, and the evaluation value calculating unit 326 may calculate the evaluation value using the determined information.

Further, in the OCT apparatus 10 according to the first embodiment, as initial positions of the OCT focus position and the coherence gate position, respective positions in acquiring tomographic information of the retina are used. Therefore, in the first embodiment, the OCT focus position and the coherence gate position are moved sequentially from the positions in acquiring the tomographic image of the retina to positions closer to the pupil side to search for the vitreous structure. In the first embodiment, the OCT apparatus 10 includes the fundus observation system, and the OCT focus controlling unit 323 may use focus information on a fundus observation image to adjust the OCT focus position to the vicinity of the retina.

However, the initial positions of the OCT focus position and the coherence gate position are not limited thereto, and may be any position, for example, positions after being moved from respective positions in acquiring the tomographic information of the retina to the pupil side by the predetermined amount, or positions used in imaging the vitreous structure last time. In this case, the lens 223 and the mirror 253 may move the OCT focus position and the coherence gate position sequentially from the initial positions to positions closer to the pupil side or the retina side to search for the vitreous structure. The setting of the initial positions of the OCT focus position and the coherence gate position at the time when the vitreous structure detection processing is started may be performed after it is determined in Step S404 that the vitreous body mode is selected, and before the processing proceeds to Step S410.

Further, in the above description, there has been described the case in which there is one evaluation value that is determined in Step S707 to be the threshold value or more, but when there are two or more vitreous structures in the imaging range of the tomographic image, there may be a plurality of evaluation values that are the threshold value or more. In this case, in Step S708, the vitreous structure determination unit 328 may set, as the vitreous structure position, a region corresponding to the largest evaluation value of the evaluation values that are the threshold value or more. As a result, there can be generated a tomographic image in which a vitreous structure that can be imaged most clearly is imaged. Moreover, OCT focus positions may be stored for the plurality of evaluation values that are the threshold value or more, and a suitable display may be provided on the screen to prompt the examiner to select the OCT focus position at which the image is to be taken. Alternatively, for example, the vitreous structure determination unit 328 may set the vitreous structure position based on an evaluation value corresponding to the OCT focus position closest to the pupil side or the retina side of the plurality of evaluation values that are the threshold value or more.

Second Embodiment

In an OCT apparatus according to a second embodiment of the present invention, the angle of incidence of the measurement light on the fundus Er of the eye E to be examined is adjusted to image the vitreous structure more appropriately.

A light intensity of light reflected or scattered by the subject to be examined of the measurement light is changed depending on the angle of incidence of the measurement light on the subject to be examined. For example, when the measurement light enters the subject to be examined substantially perpendicularly, a reflectance of the subject to be examined is increased, and return light having a higher light intensity can be obtained from the subject to be examined. Therefore, when the measurement light is allowed to enter the vitreous structure substantially perpendicularly, the light intensity of the return light from the vitreous structure can be increased. However, the vitreous structure is a mutant site of the vitreous body, and hence is varied in orientation for each vitreous structure. Therefore, even when measurement light having a particular angle of incidence is used on a different eye to be examined for measurement, there is a possibility that accuracy of detection of the vitreous structure cannot be increased.

To address this problem, in the OCT apparatus according to the second embodiment, the angle of incidence of the measurement light on the fundus Er of the eye E to be examined is adjusted such that the light intensity of the return light from the vitreous structure of the measurement light is increased, to thereby image the vitreous structure more appropriately.

Now, the OCT apparatus according to the second embodiment is described with reference to FIG. 12A to FIG. 14. A configuration of the OCT apparatus according to the second embodiment is similar to the configuration of the OCT apparatus 10 according to the first embodiment. Therefore, like reference symbols are used for the components, and a description thereof is omitted. In the following, the OCT apparatus according to the second embodiment is described mainly in terms of differences from the OCT apparatus 10 according to the first embodiment. FIG. 12A to FIG. 12F are diagrams and a graph for illustrating and showing adjustment of the angle of incidence of the measurement light on the fundus Er.

Figure 12A:
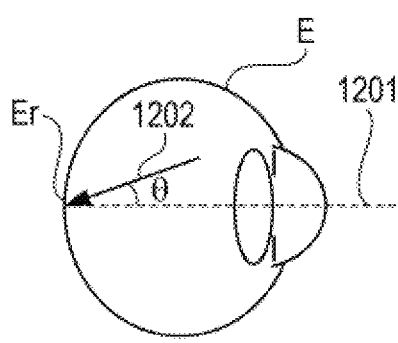
FIG. 12A is a diagram for illustrating angle-of-incidence adjustment of a second embodiment of the present invention.

First, in the following description, as illustrated in FIG. 12A, an angle of incidence θ of the measurement light on the fundus Er of the eye E to be examined is defined as an angle of incidence of measurement light 1202 with respect to a center of optical axis 1201 at the fundus Er. As described above, when the return light from the vitreous structure of measurement light enters the vitreous structure at an angle close to perpendicular, the return light has a higher light intensity. Therefore, in the second embodiment, the angle-of-incidence adjusting unit 329 of the control portion 300 adjusts the angle of incidence of the measurement light on the fundus Er such that the return light from the vitreous structure of the measurement light becomes stronger based on the tomographic image using measurement light entering the fundus Er at a different angle of incidence. In the second embodiment, the optical head drive controlling unit 312 moves the optical head 200 in a direction perpendicular to an optical axis of the measurement light to the eye E to be examined depending on a scanning direction of the measurement light, to thereby change an angle of incidence of the measurement light on the fundus Er.

Figure 12B:
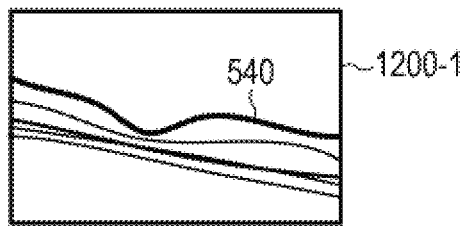
FIG. 12B is a diagram for illustrating the angle-of-incidence adjustment of the second embodiment.
Figure 12C:
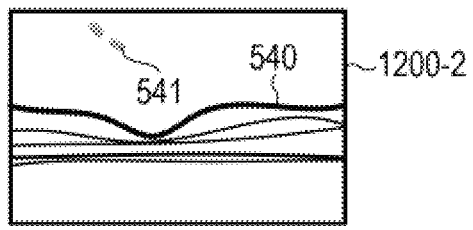
FIG. 12C is a diagram for illustrating the angle-of-incidence adjustment of the second embodiment.
Figure 12D:
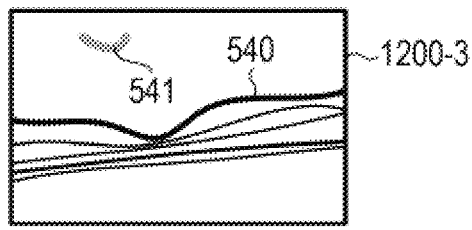
FIG. 12D is a diagram for illustrating the angle-of-incidence adjustment of the second embodiment.
Figure 12E:
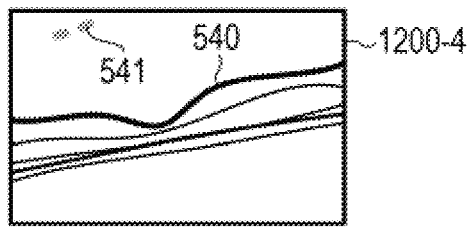
FIG. 12E is a diagram for illustrating the angle-of-incidence adjustment of the second embodiment.

In FIG. 12B to FIG. 12D, examples of tomographic images taken while changing an angle of incidence θ from −α° to +α° are illustrated. In FIG. 12B, a tomographic image 1200-1 taken at an angle of incidence θ of −α° is illustrated. In the tomographic image 1200-1, only the tomographic image 540 of the retina appears. Next, in FIG. 12C, a tomographic image 1200-2 taken at an angle of incidence θ of 0° is illustrated. In the tomographic image 1200-2, the vitreous structure 541 appears, though unclearly, above the tomographic image 540 of the retina. In FIG. 12D, a tomographic image 1200-3 taken at an angle of incidence θ of α/2° is illustrated. In the tomographic image 1200-3, the vitreous structure 541 appears clearly above the tomographic image 540 of the retina. Moreover, in FIG. 12E, a tomographic image 1200-4 taken at an angle of incidence θ of α° is illustrated. In the tomographic image 1200-4, as in the tomographic image 1200-2, the vitreous structure 541 appears, though unclearly, above the tomographic image 540 of the retina.

Figure 12F:
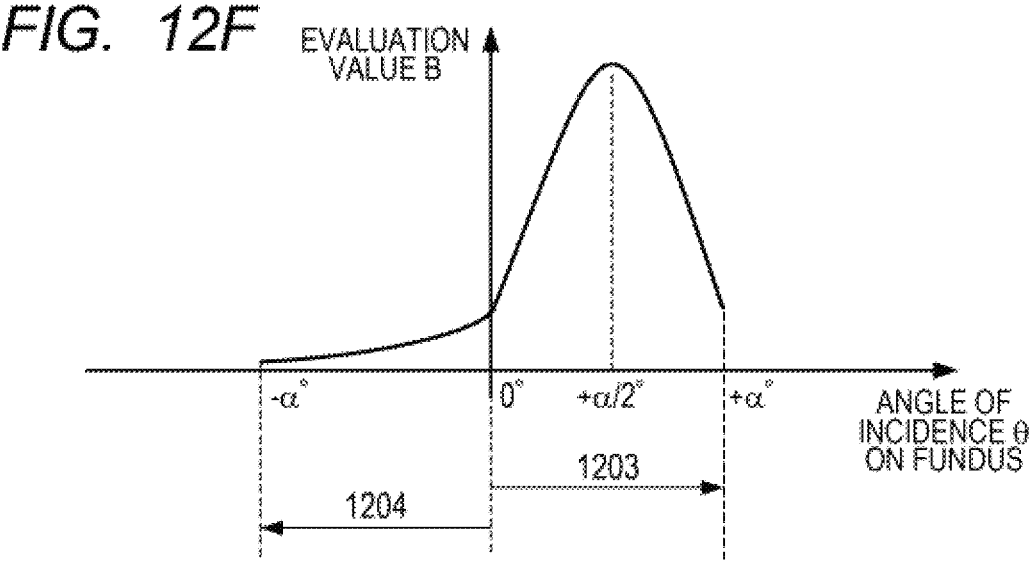
FIG. 12F is a graph for showing the angle-of-incidence adjustment of the second embodiment.

FIG. 12F is a graph of an evaluation value B of the tomographic images taken while changing an angle of incidence θ from −α° to +α°. Here, the evaluation value B is an evaluation value in each image taken while changing the angle of incidence. As in the setting of the evaluation region in the first embodiment, the region on the pupil side of the tomographic image 540 of the retina in the tomographic image is set as the evaluation region, and the evaluation value B is set as a total value of luminances in the evaluation region. Other than the total value of the luminances, the evaluation value B may be the sharpness of the luminance distribution, an average value of the luminances, a maximum value of the luminances, the contrast, or the amplitude of the particular frequency component.

Referring to FIG. 12F, with the evaluation value B being the highest when the angle of incidence θ is +α/2°, it can be seen that the measurement light enters the vitreous structure substantially perpendicularly, and the intensity of the return light from the vitreous structure of the measurement light is the highest at the time. Therefore, the angle-of-incidence adjusting unit 329 adjusts the angle of incidence θ to +α/2°, and causes the vitreous structure detection unit 324 to perform the vitreous structure detection processing. As a result, the processing of detecting the vitreous structure can be performed under the state in which the light intensity of the return light from the vitreous structure is high, and hence accuracy of detecting the vitreous structure can be increased.

When the angle of incidence θ is changed, the angle of incidence θ is changed from 0° to a predetermined angle in a plus direction as indicated by an arrow 1203 to calculate the evaluation value B at each angle of incidence. Next, the angle of incidence θ is changed from 0° to a predetermined angle in a minus direction as indicated by an arrow 1204 to calculate the evaluation value B at each angle of incidence, and the maximum value may be determined from among all the calculated evaluation values. When a peak value appears among the evaluation values B obtained while changing the angle of incidence θ in the plus direction, the angle of incidence θ at which the peak appears is defined as the maximum value, and changing of the angle of incidence in the minus direction may be emitted. Alternatively, the changing of the angle of incidence in the minus direction may be performed first. For example, the evaluation value B may be calculated at each angle of incidence while changing the angle of incidence θ from the predetermined angle in the minus direction to the predetermined angle in the plus direction, and the evaluation values B may be compared to one another to determine the maximum value. Alternatively, the angle of incidence θ may be changed from the predetermined angle in the plus direction to the predetermined angle in the minus direction.

Figure 13:
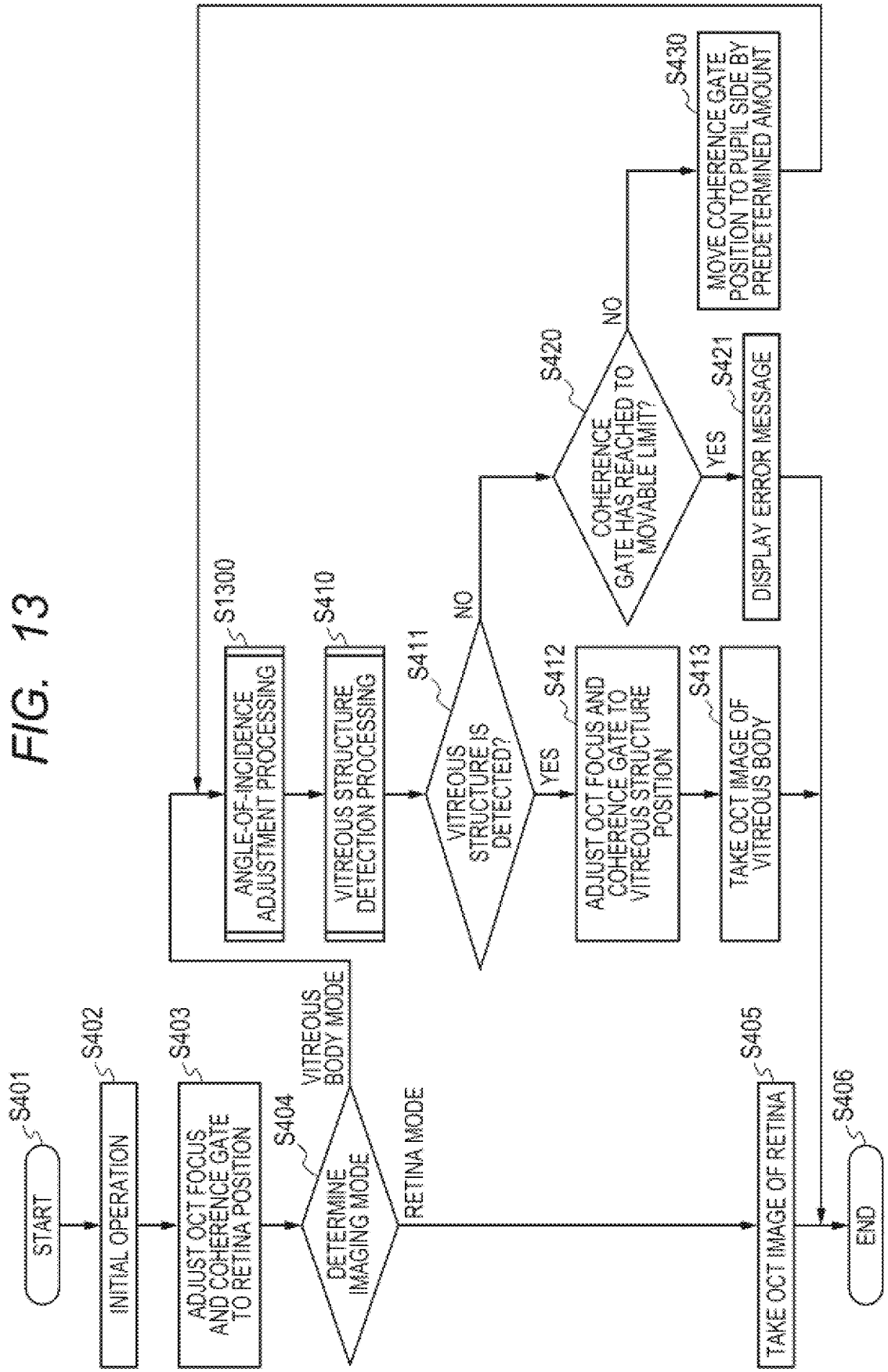
FIG. 13 is a flowchart for illustrating an imaging sequence of the second embodiment.
Figure 14:
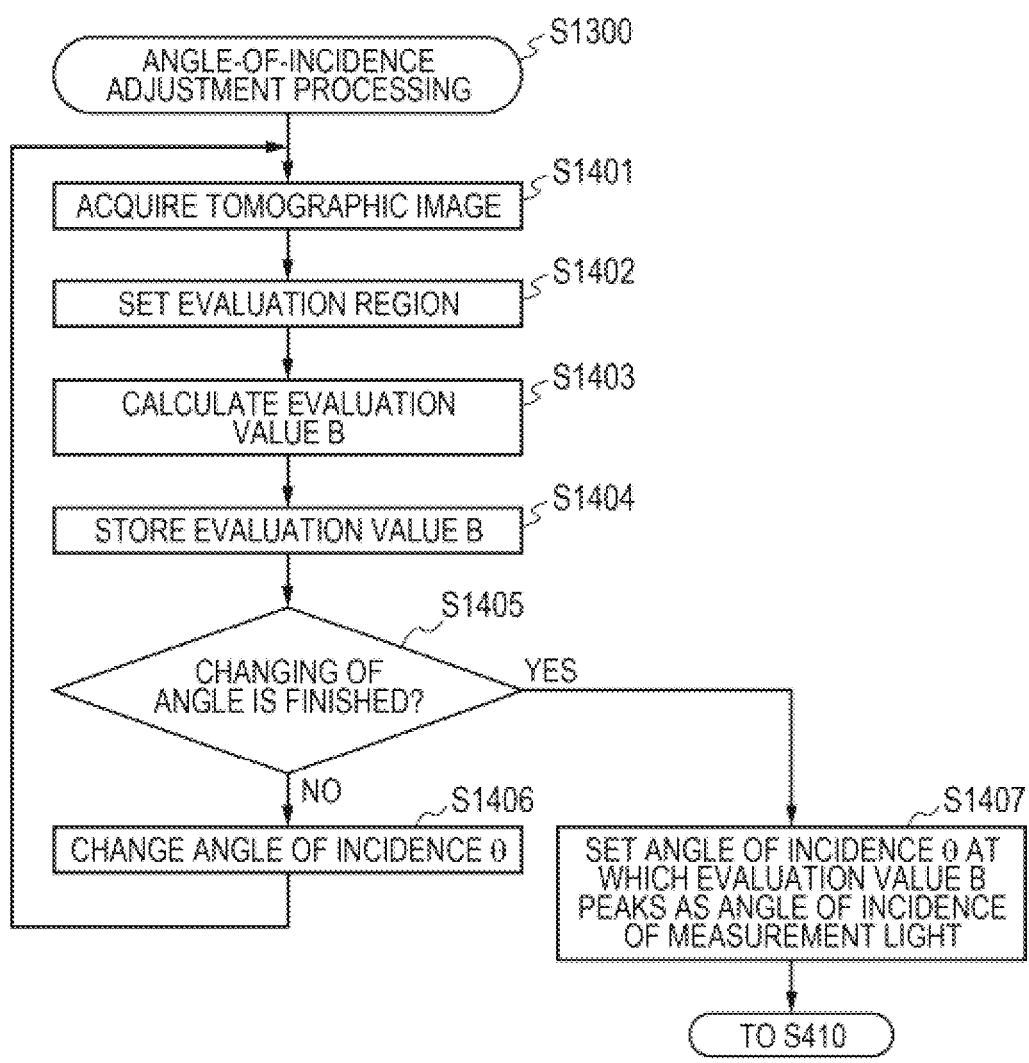
FIG. 14 is a flow chart for illustrating a sequence of angle-of-incidence adjustment processing of the second embodiment.

Next, referring to FIG. 13 and FIG. 14, an imaging sequence and angle-of-incidence adjustment processing of the second embodiment are described in further detail. FIG. 13 is a flow chart of the imaging sequence in the second embodiment. The imaging sequence other than the angle-of-incidence adjustment processing of Step S1300 is similar to the imaging sequence in the first embodiment, and hence a description thereof is omitted.

In the imaging sequence in the second embodiment, when the display controlling unit 350 determines in Step S404 that the vitreous body mode is selected, the processing proceeds to the angle-of-incidence adjustment processing of Step S1300.

FIG. 14 is a flow chart of a sequence of the angle-of-incidence adjustment processing. When the angle-of-incidence adjustment processing is started in Step S1300, the processing proceeds to Step S1401.

In Step S1401, the OCT imaging unit 320 images the eye E to be examined at a particular angle of incidence, and the angle-of-incidence adjusting unit 329 acquires the tomographic image generated by the tomographic image generation unit 321. In Step S1402, based on the tomographic image acquired by the angle-of-incidence adjusting unit 329, as in Step S702, the evaluation region for calculating the evaluation value B is set.

In Step S1403, the angle-of-incidence adjusting unit 329 calculates, as in Step S703, an evaluation value B (third evaluation value) from values of the evaluation region set in Step S1402. Here, the evaluation value B may be the total value of the luminance values in the evaluation region, the average value of the luminance values, the maximum value of the luminance values, the sharpness of the luminance distribution, the contrast, or the amplitude of the particular frequency component.

In Step S1404, the angle-of-incidence adjusting unit 329 stores the evaluation value B calculated in Step S1403 in association with the angle of incidence θ of the measurement light at the time when the tomographic image is taken. In Step S1405, it is determined whether the angle-of-incidence adjusting unit 329 has finished changing the angle of incidence θ of the measurement light to the predetermined angle. When it is determined that the angle-of-incidence adjusting unit 329 has not finished changing the angle of incidence θ to the predetermined angle, the processing proceeds to Step S1406.

In Step S1406, the angle-of-incidence adjusting unit 329 causes the optical head drive controlling unit 312 to control the electric stage 280 to move the optical head 200 in the direction perpendicular to the optical axis of the measurement light to the eye E to be examined, to thereby change the angle of incidence θ of the measurement light on the fundus Er by a predetermined amount. Thereafter, the processing returns to Step S1401.

When it is determined in Step S1405 that the angle-of-incidence adjusting unit 329 has finished changing the angle of incidence θ to the predetermined angle, the processing proceeds to Step S1407. In Step S1407, the angle-of-incidence adjusting unit 329 compares a plurality of evaluation values B based on the measurement light entering the fundus Er at different angles of incidence θ, which are stored in Step S1404, to each other to determine an angle of incidence θ at which the evaluation value B is the highest. In other words, the angle-of-incidence adjusting unit 329 determines a peak evaluation value B from among the plurality of stored evaluation values B, and identifies an angle of incidence θ corresponding to the determined evaluation value B. The angle-of-incidence adjusting unit 329 sets the identified angle of incidence θ as an angle of incidence in performing the vitreous structure detection processing, and the processing proceeds to Step S410.

In Step S410, the vitreous structure detection unit 324 causes the measurement light to enter the fundus Er at the angle of incidence adjusted in the angle-of-incidence adjustment processing of the angle-of-incidence adjusting unit 329, and performs processing similar to the vitreous structure detection processing of the first embodiment. The subsequent processing is similar to the imaging sequence in the first embodiment.

In the imaging sequence in the first embodiment, after the coherence gate position is moved in Step S430, the processing returns to Step S410, but in the imaging sequence in the second embodiment, after Step S430, the processing returns to Step S1300. As a result, in order to increase the intensity of the return light of the measurement light from a vitreous structure that newly appears in the tomographic image after the coherence gate position is moved to cause the imaging position of the tomographic image in the depth direction to move, the angle of incidence of the measurement light may be adjusted to an appropriate angle.

As described above, the OCT apparatus according to the second embodiment includes the angle-of-incidence adjusting unit 329 configured to adjust the angle of incidence of the measurement light on the fundus Er of the eye E to be examined. The angle-of-incidence adjusting unit 329 is configured to adjust the angle of incidence of the measurement light such that the light intensity of the return light from the vitreous structure of the measurement light becomes higher than a light intensity of return light from the vitreous structure of measurement light having another angle of incidence on the fundus Er. More specifically, the angle-of-incidence adjusting unit 329 is configured to calculate the evaluation values B based on tomographic information of the eye E to be examined that is acquired using the measurement light having different angles of incidence, compare the calculated evaluation values B to one other, and adjust the angle of incidence of the measurement light to the angle of incidence corresponding to the highest evaluation value B of the compared evaluation values B. Moreover, the vitreous structure detection unit 324 is configured to detect the vitreous structure using tomographic information of the eye E to be examined that is acquired using the measurement light having the adjusted angle of incidence.

With the above-mentioned configuration, the OCT apparatus according to the second embodiment can further increase the intensity of the return light from the vitreous structure of the measurement light, further facilitate the detection of the vitreous structure, and image the vitreous structure more appropriately. The angle of incidence of the measurement light on the fundus Er may be changed by the same angle, or by different angles, and the amount of change may be freely selected. Moreover, the number of evaluation values B to be compared, that is, the number of times the angle of incidence of the measurement light on the fundus Er is changed may also be freely selected.

In the OCT apparatus according to the second embodiment, the angle-of-incidence adjustment processing is performed before the vitreous structure detection processing to facilitate the detection of the vitreous structure. In contrast, the angle-of-incidence adjustment processing may be performed after the vitreous structure position is detected in the vitreous structure detection processing, and after the OCT focus position and the coherence gate position are adjusted with respect to the position. In this manner, the tomographic image of the vitreous structure can be made more clearly. Alternatively, in order to obtain both effects, the angle-of-incidence adjustment processing may be performed before and after the vitreous structure detection processing.

As described above, according to the angle-of-incidence adjustment processing of the second embodiment, the intensity of the return light from the vitreous structure of the measurement light may be further increased. Therefore, even when the tomographic image of the vitreous structure is taken after performing only angle-of-incidence adjustment without performing the vitreous structure detection processing, the intensity of the signal from the vitreous structure can be increased, and the vitreous structure can be imaged more appropriately as compared to the imaging of the vitreous structure in the related art. Moreover, in this case, only the angle-of-incidence adjustment processing is required, and when examining only the presence or absence of the vitreous structure, that is, the presence or absence of the mutant of the vitreous body, for example, the presence or absence of the mutant may be examined with a small number of processing steps and in short processing time. Moreover, even when the vitreous structure is located near the initial positions of the OCT focus position and the coherence gate position in imaging the vitreous structure, only the angle-of-incidence adjustment may be performed to image the vitreous structure more appropriately with a small number of processing steps and in short processing time. This is particularly advantageous for a case where positions in the previous imaging are used as the initial positions of the OCT focus position and the coherence gate position in performing follow-up observation of the same subject to be examined, for example.

In the second embodiment, the angle-of-incidence adjusting unit 329 adjusts the angle of incidence of the measurement light using the tomographic image generated based on the tomographic information of the eye E to be examined that is acquired by the control portion 300. However, without limiting to the tomographic image, the angle-of-incidence adjusting unit 329 may adjust the angle of incidence using, for example, tomographic information of the eye to be examined, from which the tomographic image is generated, including the output signal from the spectroscope 260, and the signal obtained by performing the suitable signal processing on the signal.

Third Embodiment

In the vitreous structure detection processing according to the first embodiment, the evaluation value is calculated while sequentially moving the OCT focus position by the predetermined amount to search for the vitreous structure. In contrast, in vitreous structure detection processing according to a third embodiment of the present invention, before the OCT focus position is moved, acquired tomographic information of the eye E to be examined is used to estimate a position at which the vitreous structure is present, and the OCT focus position is moved to the estimated position to calculate the evaluation value. As a result, the number of times the OCT focus position is moved by moving the lens 223 to search for the vitreous structure can be reduced, and the vitreous structure detection processing can be performed in shorter processing time.

Figure 15:
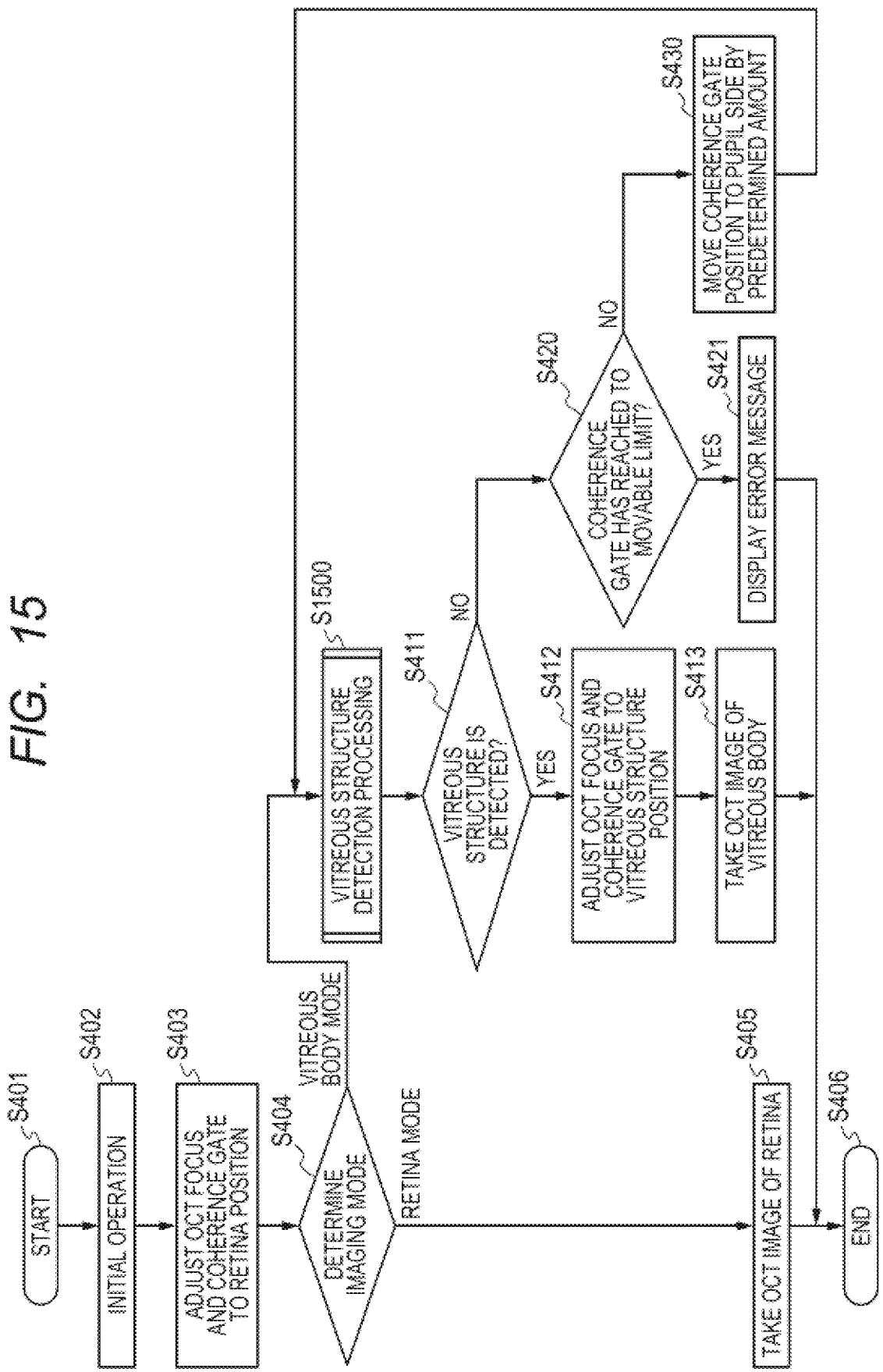
FIG. 15 is a flow chart for illustrating an imaging sequence of a third embodiment of the present invention.
Figure 16:
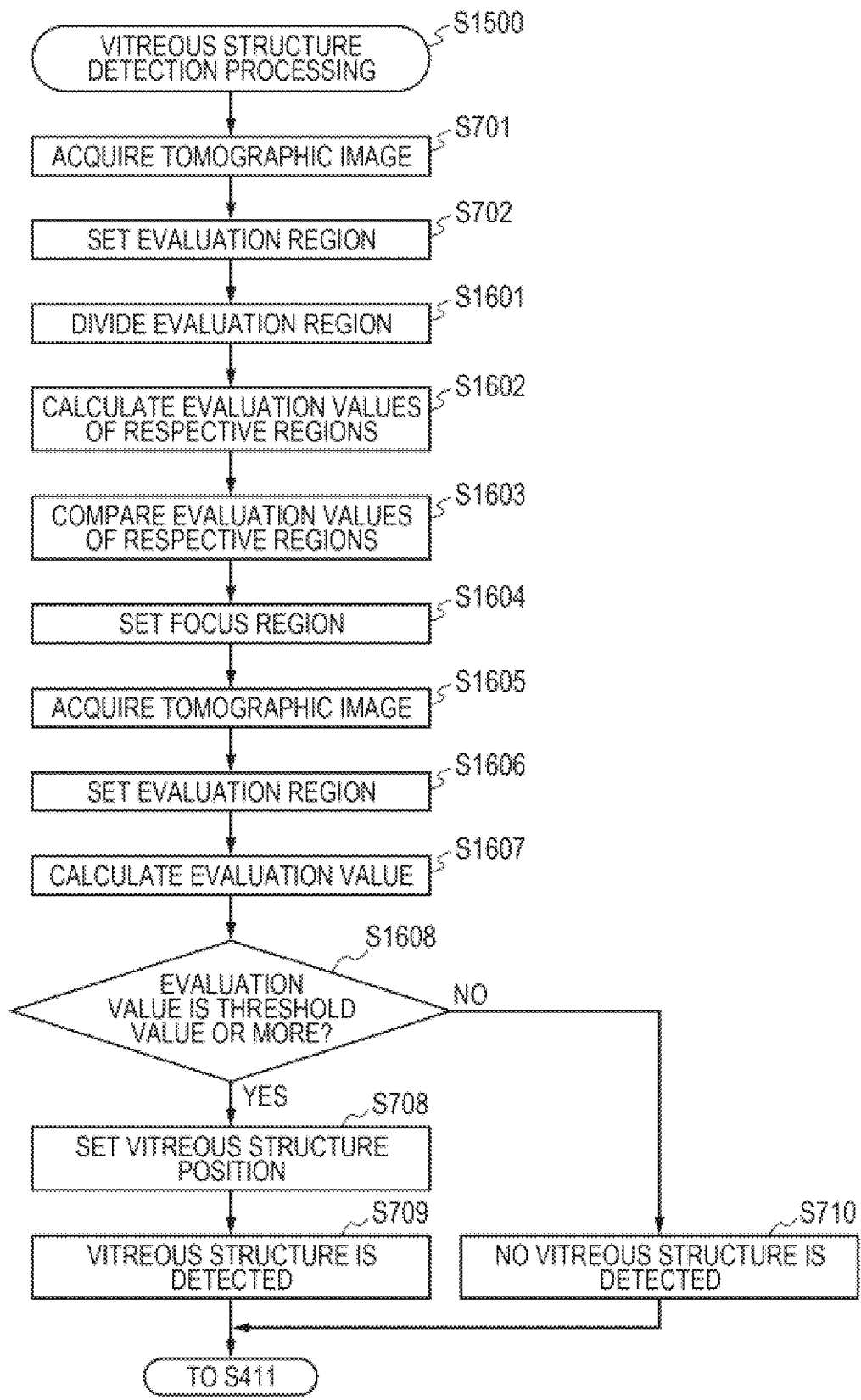
FIG. 16 is a flow chart for illustrating a sequence of vitreous structure detection processing of the third embodiment.

Now, the OCT apparatus according to the third embodiment is described with reference to FIG. 15 to FIG. 17D. A configuration of the OCT apparatus according to the third embodiment is similar to the configuration of the OCT apparatus 10 according to the first embodiment. Therefore, like reference symbols are used for the components, and a description thereof is omitted. In the following, the OCT apparatus according to the third embodiment is described mainly in terms of differences from the OCT apparatus 10 according to the first embodiment. FIG. 15 is a flow chart of an imaging sequence of the third embodiment. FIG. 16 is a flow chart of a sequence of the vitreous structure detection processing of the third embodiment. FIG. 17A to FIG. 17D are diagrams for illustrating the vitreous structure detection processing of the third embodiment.

The imaging sequence of the third embodiment is similar to the imaging sequence of the first embodiment except that, in place of the vitreous structure detection processing in Step S410 of the first embodiment, vitreous structure detection processing in Step S1500 of the third embodiment is performed. Therefore, a description of the processing other than the vitreous structure detection processing in Step S1500 is omitted.

In the imaging sequence of the third embodiment, when the display controlling unit 350 determines in Step S404 that the vitreous body mode is selected, the processing proceeds to Step S1500, and the vitreous structure detection processing of the third embodiment is started.

Figure 17A:
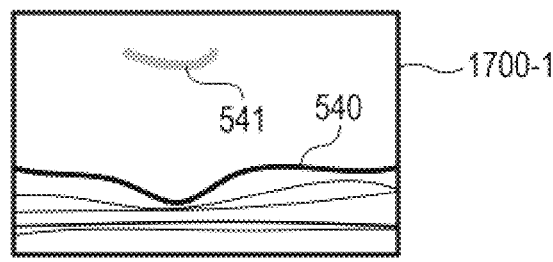
FIG. 17A is a diagram for illustrating the vitreous structure detection processing of the third embodiment.
Figure 17B:
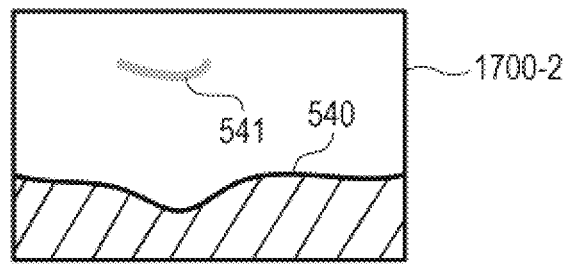
FIG. 17B is a diagram for illustrating the vitreous structure detection processing of the third embodiment.

When the vitreous structure detection processing is started, as illustrated in FIG. 16, the processing proceeds to Step S701, in which the tomographic image generation unit 321 generates a tomographic image 1700-1 illustrated in FIG. 17A, and in which the vitreous structure detection unit 324 acquires the tomographic image 1700-1. Moreover, in Step S702, the evaluation region setting unit 325 sets, as the evaluation region, a region other than the shaded portion in a tomographic image 1700-2 illustrated in FIG. 17B. The processing of Steps S701 and S702 is similar to the processing of the first embodiment, and hence details thereof are omitted.

Figure 17C:
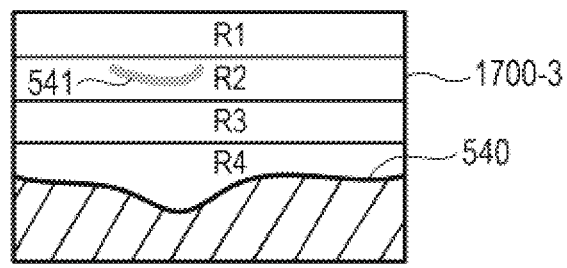
FIG. 17C is a diagram for illustrating the vitreous structure detection processing of the third embodiment.

In Step S1601, the evaluation region setting unit 325 divides the evaluation region set in step S702 into regions of predetermined ranges in the depth direction as in a tomographic image 1700-3 illustrated in FIG. 17C. In the tomographic image 1700-3, divided regions R1 to R4 are illustrated. In the third embodiment, the evaluation region is divided into four regions R1 to R4, but the number of divided regions is not limited thereto and may be freely selected. Moreover, the ranges in the depth direction of the respective regions when divided may also be freely selected. The ranges in the depth direction may be equivalent ranges for comparison of the evaluation values to be described later, but in a region adjacent to the tomographic image 540 of the retina, a region defined by the shape of the retina, for example, a region R4 may be included.

In Step S1602, the evaluation value calculating unit 326 calculates, as an evaluation value (second evaluation value) for each of the divided regions R1 to R4, a total value of luminance values in the region. Here, other than the total value of the luminance values in the region, the evaluation value may be a sharpness of a luminance distribution, an average value of the luminance values, a maximum value of the luminance values, a contrast, or an amplitude of a particular frequency component.

In Step S1603, the vitreous structure detection unit 324 compares the calculated evaluation values of the respective regions R1 to R4 to one another to determine the highest evaluation value. In Step S1604, the vitreous structure detection unit 324 estimates a region corresponding to the highest evaluation value as a position at which the vitreous structure is present, and sets the region as an OCT focus region to which the OCT focus position is to be moved. Thereafter, the OCT focus controlling unit 323 controls the motor 270 and other components to move the lens 223, to thereby adjust the OCT focus position to the set OCT focus region. In the tomographic image 1700-3, the evaluation value of the region R2 in which the vitreous structure 541 is present is the highest, and hence the OCT focus position is adjusted to a position corresponding to the region R2.

Figure 17D:
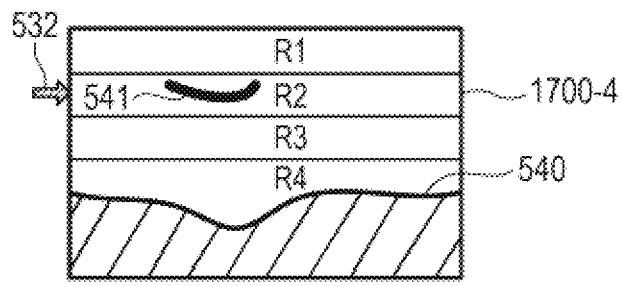
FIG. 17D is a diagram for illustrating the vitreous structure detection processing of the third embodiment.

In Step S1605, the vitreous structure detection unit 324 acquires the tomographic image generated by the tomographic image generation unit 321 under the state in which the OCT focus position is adjusted to the OCT focus region. A tomographic image 1700-4 thus acquired is illustrated in FIG. 17D. In the tomographic image 1700-4 illustrated in FIG. 17D, as indicated by the arrow 532, the OCT focus position is moved to a position corresponding to the region R2, and the vitreous structure 541 appears clearly.

In Step S1606, the vitreous structure detection unit 324 sets the evaluation region for the tomographic image acquired in step S1605. Then, in Step S1607, the evaluation value of the entire evaluation region is calculated. The processing of calculating the evaluation value in Steps S1602 and S1607 is similar to the processing in Step S703 of the first embodiment, and hence details thereof are omitted. Moreover, in the vitreous structure detection processing of the third embodiment, the coherence gate position is not moved and the imaging position is not changed in Step S701 to Step S1605, and hence the evaluation region set in Step S702 may be set at the evaluation region in Step S1606.

In Step S1608, the evaluation value of the entire evaluation region, which has been calculated in Step S1607, is compared to a predetermined threshold value, and it is determined whether the evaluation value is the threshold value or more. Thereafter, if the evaluation value is the threshold value or more, the processing proceeds to Step S708, in which the vitreous structure determination unit 328 sets the vitreous structure position. In Step S709, the vitreous structure determination unit 328 determines that the detection of the vitreous structure is complete to end the vitreous structure detection processing, and in Step S411 of FIG. 15, the processing proceeds to Step S412. Meanwhile, if the evaluation value is less than the threshold value, the processing proceeds to Step S710, in which the vitreous structure determination unit 328 determines that no vitreous structure is detected to end the vitreous structure detection processing, and in Step S411, the processing proceeds to Step S420. The subsequent processing is similar to the imaging sequence of the first embodiment, and hence a description thereof is omitted.

As described above, in the OCT apparatus according to the third embodiment, the vitreous structure detection unit 324 divides tomographic information of the eye E to be examined into pieces of information corresponding to predetermined depth ranges of the eye E to be examined, calculates the evaluation values for the respective divided pieces of information, and compares the evaluation values to one another. Thereafter, the vitreous structure detection unit 324 causes the OCT focus controlling unit 323 to change the OCT focus position of the measurement light to the position of the depth range corresponding to the highest evaluation value of the compared evaluation values. After changing the OCT focus position, the vitreous structure detection unit 324 detects the vitreous structure using the tomographic information of the eye E to be examined that is acquired by the control portion 300. In this example, the region corresponding to the highest evaluation value is determined as the position at which the vitreous structure is present, but the operation of Steps S701 to S707 may be further performed within the region to move the OCT focus position, to thereby search for the vitreous structure.

With the OCT apparatus according to the third embodiment, in the vitreous structure detection processing, the number of times the lens 223 is moved to move the OCT focus position can be reduced, and the vitreous structure detection processing can be performed in shorter processing time.

In the third embodiment, the vitreous structure detection unit 324 searches for the vitreous structure using the tomographic image generated based on the tomographic information of the eye E to be examined that is acquired by the control portion 300. However, without limiting to the tomographic image, the vitreous structure detection unit 324 may search for the vitreous structure using, for example, tomographic information of the eye to be examined, from which the tomographic image is generated, including the output signal from the spectroscope 260, and a signal obtained by performing the suitable signal processing on the signal.

Moreover, also in the third embodiment, the angle-of-incidence adjustment processing of the second embodiment may be performed to increase the intensity of the return light from the vitreous structure of the measurement light, with the result that the vitreous structure can be imaged more appropriately.

Fourth Embodiment

In the OCT apparatus according to the first embodiment, the OCT focus position and the coherence gate position are moved separately to detect the vitreous body, but in an OCT apparatus according to a fourth embodiment of the present invention, the OCT focus position and the coherence gate position are moved simultaneously to detect the vitreous body.

Figure 18:
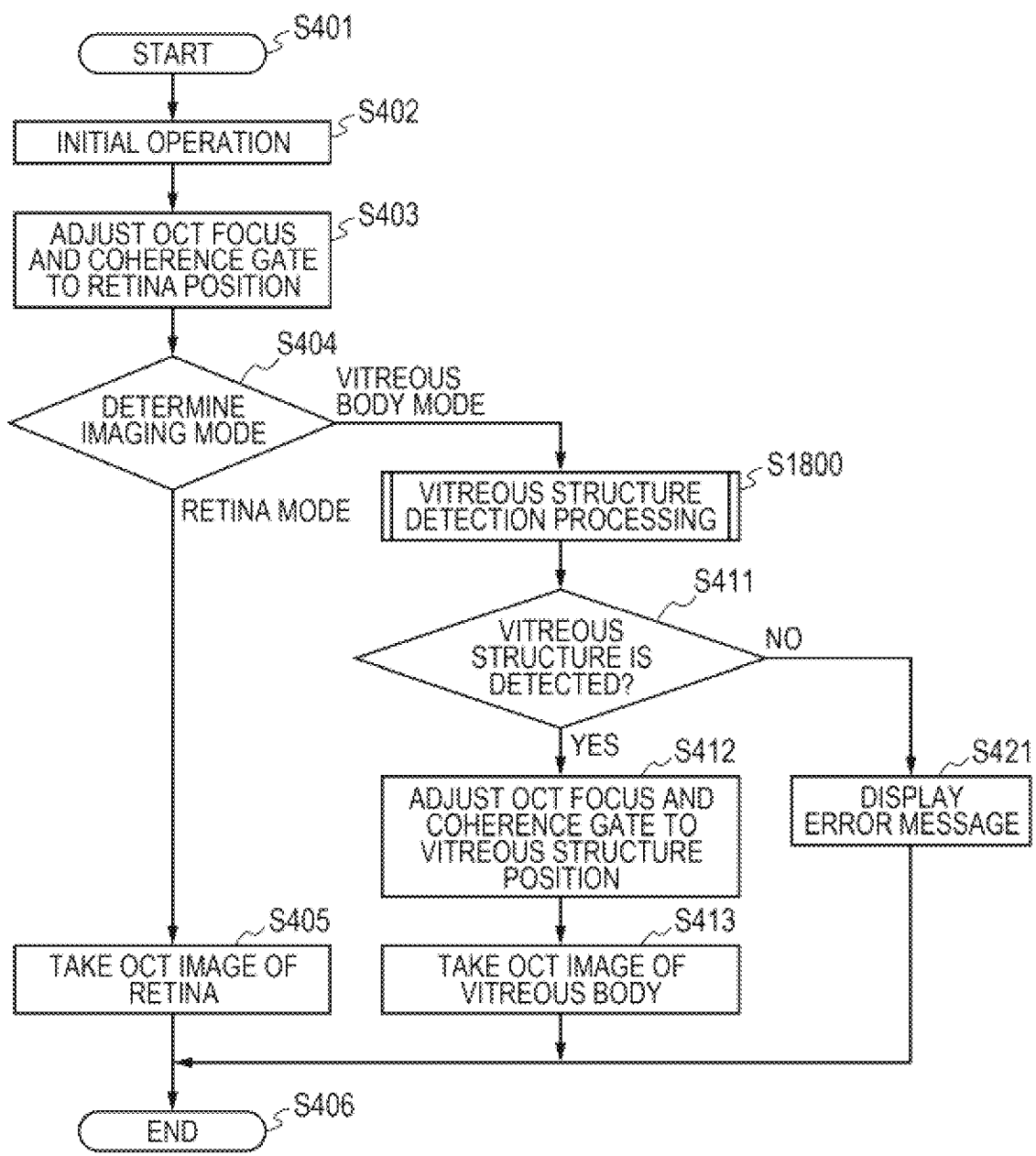
FIG. 18 is a flow chart for illustrating an imaging sequence of a fourth embodiment of the present invention.
Figure 19:
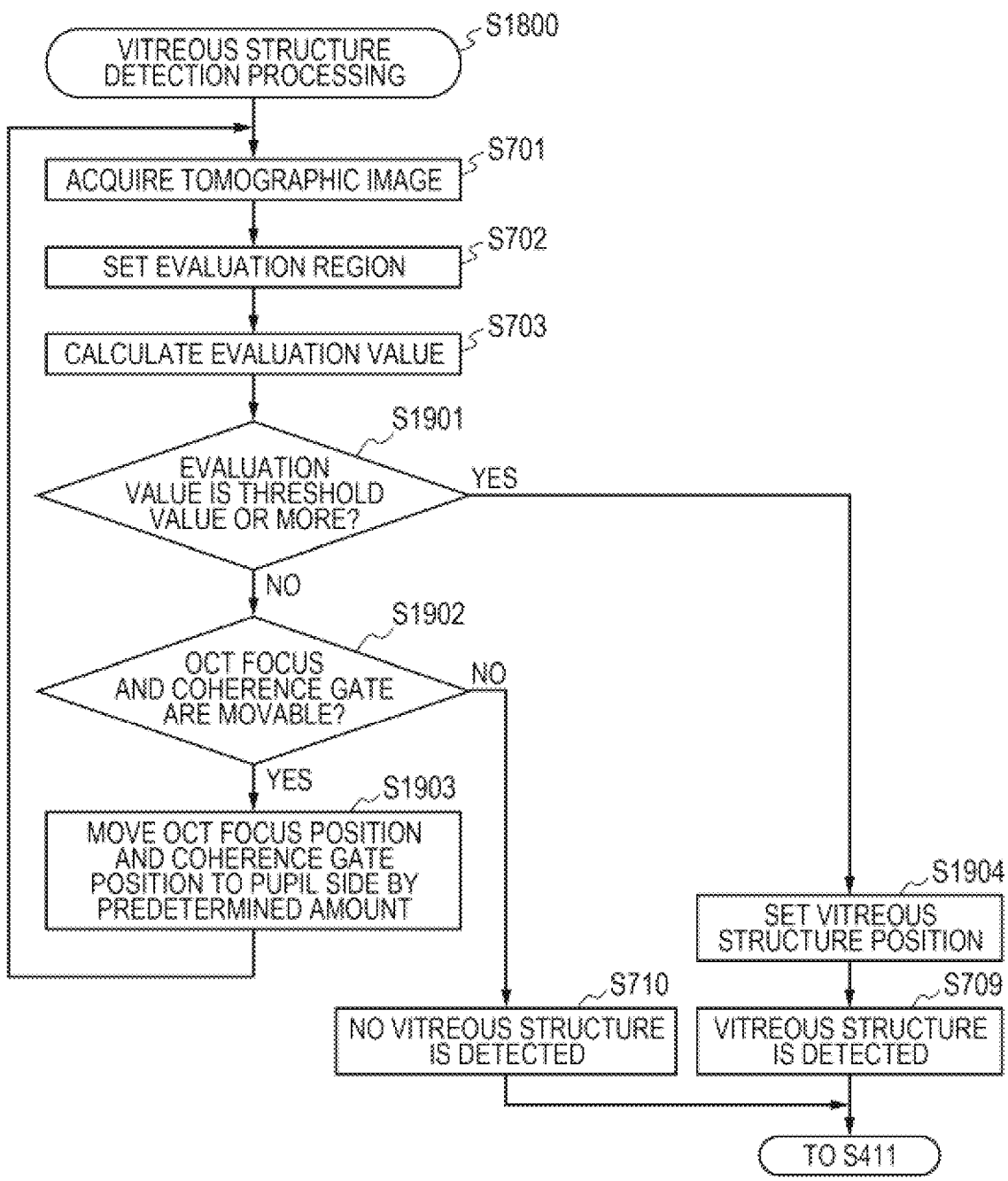
FIG. 19 is a flow chart for illustrating a sequence of vitreous structure detection processing of the fourth embodiment.

Now, the OCT apparatus according to the fourth embodiment is described with reference to FIG. 18 to FIG. 20D. A configuration of the OCT apparatus according to the fourth embodiment is similar to the configuration of the OCT apparatus 10 according to the first embodiment. Therefore, like reference symbols are used for the components, and a description thereof is omitted. In the following, the OCT apparatus according to the fourth embodiment is described mainly in terms of differences from the OCT apparatus 10 according to the first embodiment. FIG. 18 is a flow chart of an imaging sequence of the fourth embodiment. FIG. 19 is a flow chart of a sequence of vitreous structure detection processing of the fourth embodiment. FIG. 20A to FIG. 20D are diagrams for illustrating the imaging sequence for the vitreous structure of the fourth embodiment.

When the imaging sequence of the fourth embodiment is started, as in the imaging sequence of the first embodiment, the processing of Steps S402 to S404 is performed. When the display controlling unit 350 determines in Step S404 that the vitreous body mode is selected on the screen 500, the processing proceeds to Step S1800. Meanwhile, when it is determined that the retina mode is selected, as in the imaging sequence of the first embodiment, the tomographic image of the retina is taken in Step S405.

In Step S1800, there is performed an operation of detecting the vitreous structure by moving the OCT focus position and the coherence gate position simultaneously to the pupil side (vitreous body side). When the vitreous structure detection processing is started in Step S1800, as illustrated in FIG. 19, the processing proceeds to Steps S701 to S703 as in the vitreous structure detection processing of the first embodiment.

When the evaluation value is calculated in Step S703, the vitreous structure determination unit 328 compares the evaluation value to the predetermined threshold value in Step S1901, and if the evaluation value is less than the threshold value, the processing proceeds to Step S1902.

In Step S1902, the OCT focus controlling unit 323 determines whether the OCT focus position is movable. Moreover, the coherence gate controlling unit 322 determines whether the coherence gate position is movable. Here, when a drive system of each of the lens 223 and the mirror 253 has not reached its drive limit, it is determined that corresponding one of the positions is movable. Here, when none of the OCT focus position and the coherence gate position are movable, the vitreous structure determination unit 328 determines in Step S710 that no vitreous structure is detected to end the vitreous structure detection processing. Thereafter, in Step S411 of FIG. 16, the processing proceeds to Step S421. In contrast, when the OCT focus position and the coherence gate position are movable in Step S1902, the processing proceeds to Step S1903.

In Step S1903, the OCT focus controlling unit 323 and the coherence gate controlling unit 322 move the OCT focus position and the coherence gate position simultaneously to the pupil side by the predetermined amount, respectively. Then, after the movements of the OCT focus position and the coherence gate position are complete, the processing returns to Step S701.

Meanwhile, if the evaluation value is the threshold value or more in Step S1901, the processing proceeds to Step S1904, in which the vitreous structure determination unit 328 sets the OCT focus position and the coherence gate position corresponding to the evaluation value as the vitreous structure position. Thereafter, the vitreous structure detection unit 324 determines in Step S709 that the detection of the vitreous structure is complete to end the vitreous structure detection processing, and in Step S411 of FIG. 18, the processing proceeds to Step S412. Then, in Step S412, the OCT focus position and the coherence gate position are adjusted to the position at which the vitreous structure is present.

Figure 20A:
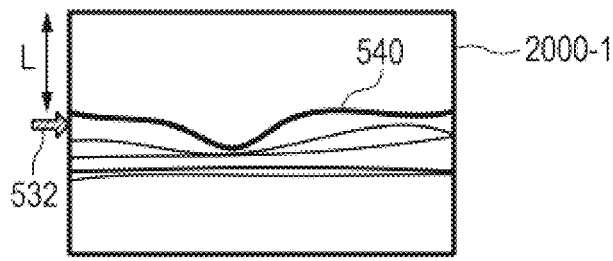
FIG. 20A is a diagram for illustrating the vitreous structure detection processing of the fourth embodiment.
Figure 20B:
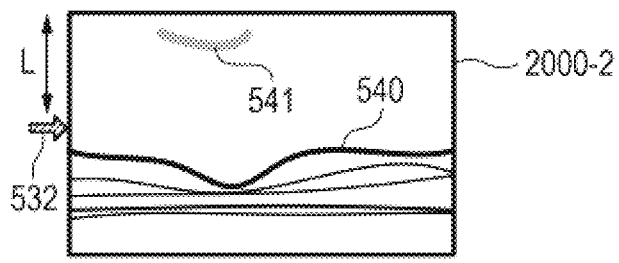
FIG. 20B is a diagram for illustrating the vitreous structure detection processing of the fourth embodiment.
Figure 20C:
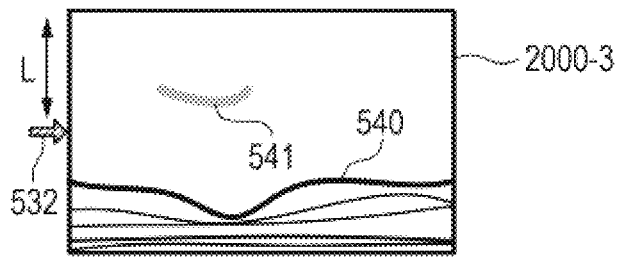
FIG. 20C is a diagram for illustrating the vitreous structure detection processing of the fourth embodiment.
Figure 20D:
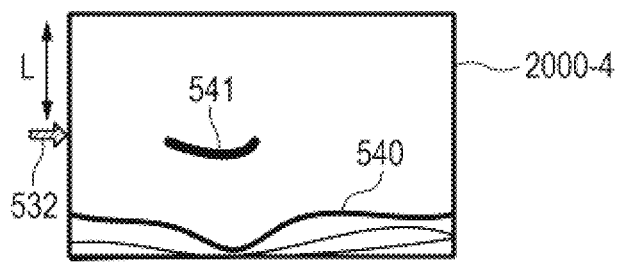
FIG. 20D is a diagram for illustrating the vitreous structure detection processing of the fourth embodiment.

Now, in FIG. 20A and FIG. 20D, there are illustrated examples of the tomographic image obtained when Steps S701 to S1903 are repeated until the vitreous structure is found, and the OCT focus position and the coherence gate position are moved simultaneously such that a distance L between those positions is maintained. In FIG. 20A to FIG. 20D, the arrow 532 indicates the OCT focus position, and the upper edge of the tomographic image indicates the coherence gate position. First, in a tomographic image 2000-1 illustrated in FIG. 20A, the OCT focus position and the coherence gate position are adjusted to the vicinity of the retina, and the vitreous structure does not appear in the tomographic image 2000-1. Therefore, the evaluation value is less than the threshold value, and the OCT focus position and the coherence gate position are moved to the pupil side by the predetermined amount in Step S1903.

A tomographic image 2000-2 illustrated in FIG. 20B is a tomographic image acquired by the OCT imaging unit 320 after the OCT focus position and the coherence gate position are moved to the pupil side by the predetermined amount in Step S1903 from the state under which the tomographic image 2000-1 is acquired. In the tomographic image 2000-2, the vitreous structure 541 appears in the tomographic image, but is not in the OCT focus, with the result that the evaluation value is less than the threshold value. Therefore, the OCT focus position and the coherence gate position are moved again to the pupil side by the predetermined amount in Step S1903.

Thereafter, a tomographic image 2000-3 illustrated in FIG. 20C is acquired, but the evaluation value is less than the threshold value as with the tomographic image 2000-2. Therefore, in Step S1903, the OCT focus position and the coherence gate position are moved again to the pupil side by the predetermined amount.

In FIG. 20D, there is illustrated a tomographic image 2000-4 acquired when the OCT focus position and the coherence gate position are further moved to the pupil side by the predetermined amount from the state under which the tomographic image 2000-3 is taken. In the tomographic image 2000-4, the vitreous structure 541 is in the OCT focus, and hence the evaluation value is the threshold value or more. Therefore, the vitreous structure determination unit 328 sets the OCT focus position and the coherence gate position at the time when the tomographic image 2000-4 is taken as the vitreous structure position, and the processing proceeds to processing of imaging the vitreous structure.

As described above, in the OCT apparatus of the fourth embodiment, the coherence gate controlling unit 322 moves the coherence gate position in synchronization with the change of the OCT focus position by the OCT focus controlling unit 323. At this time, the coherence gate controlling unit 322 changes the coherence gate position in the same direction as a direction of the change of the OCT focus position. If an evaluation value calculated thereafter does not exceed the threshold value, the coherence gate position is changed again by the coherence gate controlling unit 322 in synchronization with a further change of the OCT focus position. Even when the OCT focus position and the coherence gate position are moved simultaneously as in the OCT apparatus of the fourth embodiment, the vitreous structure can be detected appropriately, and hence the vitreous structure can be imaged appropriately.

In the example described above, the OCT focus position and the coherence gate position are moved simultaneously such that the distance L between those positions is maintained for the purpose of ensuring that the OCT focus position is always at the same position in the tomographic image. Therefore, the distance L does not always need to be maintained depending on a desired configuration, and the distance L may be changed during the adjustments depending on speeds of the individual motors. Moreover, in the example described above, it is determined that the vitreous structure is detected as soon as the evaluation value becomes the threshold value or more, but even after the evaluation value becomes the threshold value or more, the OCT focus position and the coherence gate position may be moved continuously to find the peak of the evaluation values before the determination is made.

In the fourth embodiment, the vitreous structure detection unit 324 searches for the vitreous structure using the tomographic image generated based on the tomographic information of the eye E to be examined that is acquired by the control portion 300. However, without limiting to the tomographic image, the vitreous structure detection unit 324 may search for the vitreous structure using, for example, tomographic information of the eye to be examined, from which the tomographic image is generated, including the output signal from the spectroscope 260, and a signal obtained by performing the suitable signal processing on the signal.

Moreover, in the OCT apparatus 10 of the fourth embodiment, as the initial positions of the OCT focus position and the coherence gate position, respective positions at the time when tomographic information of the retina is acquired are used. However, the initial positions of the OCT focus position and the coherence gate position are not limited thereto, and may be any position, for example, positions obtained after movements from the respective positions at the time when the tomographic information of the retina is acquired to the pupil side by the predetermined amount, and positions used when the vitreous structure is imaged last time. In this case, the lens 223 and the mirror 253 may sequentially move the OCT focus position and the coherence gate position from the initial positions to positions closer to the pupil side or the retina side to search for the vitreous structure.

Moreover, also in the fourth embodiment, the angle-of-incidence adjustment processing of the second embodiment may be performed to increase the intensity of the return light from the vitreous structure of the measurement light, with the result that the vitreous structure can be imaged more appropriately.

In the first to fourth embodiments, imaging of the vitreous structure by the OCT apparatus is described. In relation thereto, it can be contemplated to image the vitreous structure by the OCT apparatus for the follow-up observation of the subject to be examined. In this case, imaging parameters of the vitreous structure are stored in association with identification information (patient ID) of the subject to be examined such that the vitreous structure can be imaged quickly using the imaging parameters the next time the examination (imaging) is performed. More specifically, the OCT focus position, the coherence gate position, the angle of incidence of the measurement light on the fundus Er, and other parameters at the time when the vitreous structure is imaged are stored in the storage unit 340 in association with the identification information (patient ID) of the subject to be examined. Then, the next time the examination is performed, the OCT imaging unit 320 acquires from the storage unit 340 and uses those imaging parameters associated with the identification information of the subject to be examined, with the result that an image that is easily compared in the follow-up observation can be taken easily. In this case, the OCT imaging unit 320 serves as a parameter acquisition unit, which is configured to acquire the imaging parameters.

Those stored imaging parameters may be used as initial values of the imaging parameters the next time the examination is performed, or may be used as fixed parameters for the follow-up observation of the subject to be examined. Moreover, the present invention is not limited to the configuration in which those imaging parameters for the follow-up observation are stored in the storage unit 340. For example, there may be adopted a configuration in which the imaging parameters at the time when the vitreous structure is imaged may be stored in a server in the Internet, a wide area network (WAN), or a local area network (LAN) that is connected wiredly or wirelessly to the OCT apparatus, and in which the OCT imaging unit 320 acquires those imaging parameters from the server the next time the follow-up observation is performed.

In the first to fourth embodiments, as a member configured to move the coherence gate position, the mirror 253 is moved, but a configuration of the member is not limited thereto. Any member configured to move the coherence gate position may be used as long as one of the optical path length of the measurement light and the optical path length of the reference light can be changed, to thereby change the difference in optical path length between the measurement light and the reference light. Therefore, the member may be formed of any optical member or other member configured to change the optical path length of the measurement light.

Further, a fiber optic system using a coupler is used as a splitting unit, but a spatial optical system using a collimator and a beam splitter may be used. Moreover, the configuration of the imaging apparatus portion 100 is not limited to the above-mentioned configuration, and a part of the configuration included in the imaging apparatus portion 100 may be formed separately from the imaging apparatus portion 100. Further, in the embodiments described above, as a unit configured to change the angle of incidence of the measurement light on the fundus of the eye to be examined, the optical head 200 is moved with respect to the eye E to be examined by the electric stage 280, but the configuration with which the angle of incidence of the measurement light is changed is not limited thereto. For example, an optical member configured to move the optical axis of the measurement light, for example, a plane-parallel plate, may be provided in the optical path of the measurement light, and the optical member may be controlled by the control portion 300 to control the angle of incidence of the measurement light on the fundus Er.

Moreover, a configuration of a Michelson interferometer is used as an interference optical system of the OCT apparatus 10, but the configuration of the interference optical system is not limited thereto. For example, the interference optical system of the OCT apparatus 10 may have a configuration of a Mach-Zehnder interferometer.

Further, as the OCT apparatus, a spectral-domain OCT (SD-OCT) apparatus using an SLD as a light source is described, but the configuration of the OCT apparatus according to the present invention is not limited thereto. For example, the present invention may be applied to an OCT apparatus of any other type, for example, a swept source OCT (SS-OCT) apparatus using a wavelength swept light source, which is capable of sweeping a wavelength of emitted light.

The present invention is described above referring to the embodiments. However, the present invention is not limited to the above-mentioned embodiments. The present invention also encompasses the invention modified within a scope not deviated from the present invention, and the invention equivalent to the present invention. Further, the above-mentioned embodiments and modifications may be combined with each other as appropriate within the scope not deviated from the present invention.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-241022, filed Dec. 13, 2016, which is hereby incorporated by reference herein in its entirety.

What is claimed is:

1. An ophthalmologic apparatus, comprising:
   an acquisition unit configured to acquire tomographic information of an eye to be examined using information on interference light between return light from the eye to be examined, which is irradiated with measurement light, and reference light;
   an optical path length difference controlling unit configured to control a difference in optical path length between the measurement light and the reference light;
   an in-focus position controlling unit configured to control an in-focus position of the measurement light; and a vitreous structure detection unit configured to detect a vitreous structure of the eye to be examined using tomographic information of the eye to be examined that is acquired after at least one of the difference in optical path length and the in-focus position is controlled, wherein the acquisition unit is configured to acquire tomographic information of the vitreous structure after the difference in optical path length and the in-focus position are controlled based on positional information of the detected vitreous structure.

2. An ophthalmologic apparatus according to claim 1, wherein the vitreous structure detection unit is configured to detect the vitreous structure using tomographic information of the eye to be examined that is acquired each time the in-focus position is changed sequentially.

3. An ophthalmologic apparatus according to claim 1, wherein the optical path length difference controlling unit is configured to change the difference in optical path length in synchronization with a change of the in-focus position by the in-focus position controlling unit.

4. An ophthalmologic apparatus according to claim 1, wherein, if the in-focus position is changed by a predetermined amount, the optical path length difference controlling unit changes the difference in optical path length such that tomographic information of the eye to be examined after being moved in a same direction as a direction of the change of the in-focus position in a depth direction of the eye to be examined is obtained.

5. An ophthalmologic apparatus according to claim 1, wherein the vitreous structure detection unit is configured to:
calculate a first evaluation value using information corresponding to a vitreous region of the eye to be examined of the tomographic information of the eye to be examined; and
determine that the vitreous structure is detected if the first evaluation value is a threshold value or more.

6. An ophthalmologic apparatus according to claim 5, wherein the vitreous structure detection unit is configured to:
divide the tomographic information of the eye to be examined into pieces of information respectively corresponding to predetermined depth ranges of the eye to be examined;
calculate second evaluation values for the divided pieces of information, respectively, to compare the second evaluation values to one another;
cause the in-focus position controlling unit to change the in-focus position of the measurement light to a position of one of the predetermined depth ranges that corresponds to a highest evaluation value of the second evaluation values compared to one another; and
detect the vitreous structure using the tomographic information of the eye to be examined that is acquired by the acquisition unit.

7. An ophthalmologic apparatus according to claim 5, wherein the vitreous structure detection unit is configured to, if the first evaluation value does not exceed the threshold value:
cause the in-focus position controlling unit to change the in-focus position by a predetermined amount;
cause the optical path length difference controlling unit to change the difference in optical path length by a predetermined amount such that tomographic information of the eye to be examined after being moved in a same direction as a direction of the change of the in-focus position in a depth direction of the eye to be examined is obtained; and
detect the vitreous structure using the tomographic information of the eye to be examined that is acquired by the acquisition unit.

8. An ophthalmologic apparatus according to claim 5, wherein the optical path length difference controlling unit is configured to change the difference in optical path length in synchronization with a change of the in-focus position by the in-focus position controlling unit, and
wherein the vitreous structure detection unit is configured to, if the first evaluation value does not exceed the threshold value: cause the in-focus position controlling unit to change the in-focus position; and cause the optical path length difference controlling unit to change the difference in optical path length again in synchronization with the change of the in-focus position.

9. An ophthalmologic apparatus according to claim 5, wherein the first evaluation value is calculated using at least one of a superimposed image generated based on the tomographic information of the eye to be examined, and a total luminance, an average luminance, a maximum luminance, a contrast, and an amplitude of a particular frequency component of a tomographic image generated based on the tomographic information of the eye to be examined.

10. An ophthalmologic apparatus according to claim 1, further comprising an angle-of-incidence adjusting unit configured to adjust an angle of incidence of the measurement light on a fundus of the eye to be examined,
wherein the angle-of-incidence adjusting unit is configured to adjust the angle of incidence of the measurement light such that a light intensity of return light from the vitreous structure of the measurement light becomes higher than a light intensity of return light from the vitreous structure of measurement light having another angle of incidence on the fundus, and
wherein the vitreous structure detection unit is configured to detect the vitreous structure using tomographic information of the eye to be examined that is acquired using the measurement light having the adjusted angle of incidence.

11. An ophthalmologic apparatus according to claim 1, wherein the optical path length difference controlling unit is configured to change the difference in optical path length such that tomographic information of the eye to be examined that is closer to a pupil side is acquired, and
wherein the in-focus position controlling unit is configured to change the in-focus position such that the in-focus position is moved toward the pupil side.

12. An ophthalmologic apparatus according to claim 1, further comprising a parameter acquisition unit configured to acquire information on a subject to be examined, and a parameter including at least one of the difference in optical path length, the in-focus position, and an angle of incidence at a time of acquiring the tomographic information of the vitreous structure by the acquisition unit,
wherein the acquired parameter is used if information on the vitreous structure of the subject to be examined is to be acquired again.

13. An ophthalmologic apparatus according to claim 1, further comprising a contrast adjusting unit configured to adjust a contrast of a tomographic image generated based on the tomographic information of the eye to be examined,
wherein the vitreous structure detection unit is configured to detect the vitreous structure using the tomographic image having the adjusted contrast.

14. An ophthalmologic apparatus according to claim 1, wherein the vitreous structure detection unit is configured to issue an alarm if the vitreous structure is not detected.

15. An ophthalmologic apparatus according to claim 1, wherein at least one of an in-focus position and a difference in optical path length corresponding to any of a plurality of evaluation values obtained using a plurality of pieces of tomographic information of the eye to be examined, which correspond to at least one of different in-focus positions and different differences in optical path, is used as the positional information of the detected vitreous structure.

16. An ophthalmologic apparatus according to claim 15, wherein at least one of an in-focus position and a difference in optical path length corresponding to an evaluation value of the plurality of evaluation values, which is higher than a threshold value, is used as the positional information.

17. An ophthalmologic apparatus according to claim 1, wherein the acquisition unit is configured to acquire a plurality of pieces of the tomographic information of the vitreous structure, and wherein a plurality of tomographic images generated based on the plurality of pieces of the tomographic information of the vitreous structure are used to generate one tomographic image.

18. An ophthalmologic apparatus according to claim 17, wherein the one tomographic image is generated by averaging the plurality of tomographic images.

19. An ophthalmologic apparatus according to claim 1, wherein a contrast of a tomographic image generated based on the tomographic information of the vitreous structure is adjusted so that the vitreous structure becomes clearer.

20. An ophthalmologic imaging method, comprising:

acquiring tomographic information of an eye to be examined using information on interference light between return light from the eye to be examined, which is irradiated with measurement light, and reference light;

detecting a vitreous structure of the eye to be examined using tomographic information of the eye to be examined that is acquired after at least one of a difference in optical path length between the measurement light and the reference light, and an in-focus position of the measurement light is controlled; and acquiring tomographic information of the vitreous structure after the difference in optical path length and the in-focus position are controlled based on positional information of the detected vitreous structure.

21. A non-transitory computer-readable storage medium storing a program for causing a computer to execute the method according to claim 20.

* * * * *